(12) United States Patent
Narasimhan et al.

(10) Patent No.: US 12,268,484 B2
(45) Date of Patent: Apr. 8, 2025

(54) DIGITAL ARTERY BLOOD PRESSURE MONITOR

(71) Applicant: Verily Life Sciences LLC, South San Francisco, CA (US)

(72) Inventors: Ravi Narasimhan, Sunnyvale, CA (US); Tushar Parlikar, Somerville, MA (US); Todd Whitehurst, Redwood City, CA (US)

(73) Assignee: Verily Life Sciences LLC, Dallas, TX (US)

( * ) Notice: Subject to any disclaimer, the term of this patent is extended or adjusted under 35 U.S.C. 154(b) by 1309 days.

(21) Appl. No.: 16/923,906

(22) Filed: Jul. 8, 2020

(65) Prior Publication Data

US 2020/0337571 A1 Oct. 29, 2020

Related U.S. Application Data

(62) Division of application No. 15/414,354, filed on Jan. 24, 2017, now Pat. No. 10,874,307.

(51) Int. Cl.
*A61B 5/022* (2006.01)
*A61B 5/00* (2006.01)
(Continued)

(52) U.S. Cl.
CPC ........ *A61B 5/02241* (2013.01); *A61B 5/0225* (2013.01); *A61B 5/6826* (2013.01); *A61B 5/021* (2013.01); *A61B 5/02108* (2013.01); *A61B 5/02125* (2013.01); *A61B 5/02225* (2013.01); *A61B 5/024* (2013.01); *A61B 5/029* (2013.01);
(Continued)

(58) Field of Classification Search
None
See application file for complete search history.

(56) References Cited

U.S. PATENT DOCUMENTS 4,429,700 A 2/1984 Thees et al.
4,771,790 A 9/1988 Yamasawa et al.
(Continued)

FOREIGN PATENT DOCUMENTS

CN 101730502 A 6/2010
CN 101730841 A 6/2010
(Continued)

OTHER PUBLICATIONS

Calhoon, J., "Tactile sensors support next generation medical devices", published Aug. 25, 2016, 3 pages.
(Continued)

*Primary Examiner* — Michael R Bloch
(74) *Attorney, Agent, or Firm* — Christensen O'Connor Johnson Kindness PLLC

(57) ABSTRACT

An example of a digital artery blood pressure monitor may include a tactile sensor array disposed on an inner surface of a cuff, the tactile sensor array including a plurality of capacitive sensors to detect pressure changes within a digital artery of a finger due to blood flow, where the pressure changes cause changes to capacitance values of one or more capacitive sensors of the tactile sensor array, and control circuitry coupled to the tactile sensor array to receive the capacitance values from the tactile sensor array, and determine a blood pressure based on the capacitance values.

20 Claims, 10 Drawing Sheets

(51) Int. Cl.
*A61B 5/0225* (2006.01)
*A61B 5/021* (2006.01)
*A61B 5/024* (2006.01)
*A61B 5/029* (2006.01)

(52) U.S. Cl.
CPC ..... *A61B 5/7278* (2013.01); *A61B 2562/0247* (2013.01); *A61B 2562/043* (2013.01); *A61B 2562/046* (2013.01)

(56) References Cited

U.S. PATENT DOCUMENTS

| | | | |
|---|---|---|---|
| 4,821,734 | A | 4/1989 | Koshino |
| 5,107,848 | A | 4/1992 | Oku |
| 5,111,817 | A * | 5/1992 | Clark ................ A61B 5/02007 600/323 |
| 5,152,296 | A | 10/1992 | Simons |
| 5,218,966 | A | 6/1993 | Yamasawa |
| 6,280,390 | B1 | 8/2001 | Akselrod et al. |
| 6,533,729 | B1 | 3/2003 | Khair et al. |
| 6,537,271 | B1 | 3/2003 | Murray et al. |
| 6,669,648 | B1 | 12/2003 | Fortin et al. |
| 6,699,199 | B2 | 3/2004 | Asada et al. |
| 7,306,563 | B2 | 12/2007 | Huang |
| 7,344,502 | B2 | 3/2008 | Tanabe |
| 7,674,231 | B2 | 3/2010 | McCombie et al. |
| 8,251,903 | B2 | 8/2012 | LeBoeuf et al. |
| 8,343,062 | B2 | 1/2013 | Fortin et al. |
| 8,814,800 | B2 | 8/2014 | Fortin et al. |
| 9,345,424 | B2 | 5/2016 | Wang et al. |
| 9,480,423 | B2 | 11/2016 | Kim et al. |
| 9,554,484 | B2 | 1/2017 | Rogers et al. |
| 10,531,802 | B2 | 1/2020 | Adi et al. |
| 2002/0177781 | A1 | 11/2002 | Amano |
| 2002/0188206 | A1 | 12/2002 | Davis et al. |
| 2003/0163053 | A1 | 8/2003 | Ogura et al. |
| 2004/0044288 | A1 | 3/2004 | Gorenberg et al. |
| 2004/0077955 | A1 | 4/2004 | Kawanishi et al. |
| 2004/0116787 | A1 | 6/2004 | Schnall |
| 2004/0181254 | A1 | 9/2004 | Choi et al. |
| 2005/0096552 | A1 | 5/2005 | Law et al. |
| 2005/0187438 | A1* | 8/2005 | Xie ........................ G01N 21/65 600/473 |
| 2005/0215989 | A1 | 9/2005 | Abboud et al. |
| 2005/0228297 | A1 | 10/2005 | Banet et al. |
| 2005/0228298 | A1 | 10/2005 | Banet et al. |
| 2006/0161200 | A1 | 7/2006 | Fallah |
| 2006/0253041 | A1 | 11/2006 | Shin et al. |
| 2007/0118045 | A1 | 5/2007 | Naghavi et al. |
| 2007/0167844 | A1 | 7/2007 | Asada et al. |
| 2007/0203416 | A1 | 8/2007 | Lowe |
| 2008/0039731 | A1 | 2/2008 | Mccombie et al. |
| 2008/0071180 | A1* | 3/2008 | Borgos ................ A61B 5/7239 600/490 |
| 2008/0081963 | A1 | 4/2008 | Naghavi et al. |
| 2008/0214942 | A1 | 9/2008 | Oh et al. |
| 2008/0234788 | A1 | 9/2008 | Wasowski |
| 2008/0287812 | A1 | 11/2008 | Parlikar et al. |
| 2009/0143655 | A1 | 6/2009 | Shani |
| 2009/0209870 | A1* | 8/2009 | Tanabe .................... G01L 1/144 600/500 |
| 2009/0281399 | A1* | 11/2009 | Keel ................ A61B 5/02158 600/513 |
| 2009/0306487 | A1 | 12/2009 | Crowe et al. |
| 2010/0106029 | A1* | 4/2010 | Fraden ............... A61B 5/02208 600/490 |
| 2010/0168531 | A1 | 7/2010 | Shaltis et al. |
| 2010/0286538 | A1* | 11/2010 | Kim ................... A61B 5/02108 600/493 |
| 2011/0015504 | A1 | 1/2011 | Yoo |
| 2011/0054330 | A1 | 3/2011 | Pfeiffer et al. |
| 2011/0146400 | A1 | 6/2011 | Humbert et al. |
| 2012/0059267 | A1 | 3/2012 | Lamego et al. |
| 2012/0238887 | A1* | 9/2012 | Gerdt ................ A61B 5/6826 600/499 |
| 2013/0144176 | A1 | 6/2013 | Lec |
| 2013/0317303 | A1 | 11/2013 | Deshmukh et al. |
| 2013/0345688 | A1 | 12/2013 | Babkin et al. |
| 2014/0114152 | A1 | 4/2014 | Fournier |
| 2014/0323891 | A1 | 10/2014 | Sterling et al. |
| 2015/0011906 | A1 | 1/2015 | Wallach |
| 2015/0157247 | A1 | 6/2015 | Weinstein et al. |
| 2015/0272452 | A1 | 10/2015 | Mullin et al. |
| 2015/0272455 | A1 | 10/2015 | Krasnov et al. |
| 2015/0274505 | A1 | 10/2015 | Molfese et al. |
| 2015/0305632 | A1 | 10/2015 | Najarian et al. |
| 2015/0327784 | A1 | 11/2015 | Lading et al. |
| 2015/0374249 | A1 | 12/2015 | Elliott et al. |
| 2016/0113589 | A1 | 4/2016 | Yoon |
| 2016/0120420 | A1 | 5/2016 | Liedl et al. |
| 2016/0198955 | A1 | 7/2016 | Fortin |
| 2016/0317060 | A1 | 11/2016 | Connor |
| 2017/0055854 | A1 | 3/2017 | Choucair et al. |
| 2017/0086686 | A1* | 3/2017 | Narasimhan ....... A61B 5/02141 |
| 2017/0135740 | A1 | 5/2017 | Sara et al. |
| 2017/0188975 | A1 | 7/2017 | Banet et al. |
| 2017/0238878 | A1 | 8/2017 | Lading et al. |
| 2017/0360306 | A1 | 12/2017 | Narasimhan et al. |
| 2017/0360313 | A1 | 12/2017 | Baek et al. |
| 2018/0028777 | A1 | 2/2018 | Cheng |
| 2018/0046281 | A1 | 2/2018 | Pi et al. |
| 2018/0078154 | A1 | 3/2018 | Knickerbocker et al. |
| 2018/0078155 | A1 | 3/2018 | Baek et al. |
| 2018/0103856 | A1* | 4/2018 | Murray ............. A61B 5/02233 |
| 2018/0192900 | A1 | 7/2018 | Wei |
| 2018/0206746 | A1 | 7/2018 | Narasimhan et al. |
| 2018/0235468 | A1 | 8/2018 | Khachaturian et al. |
| 2018/0310835 | A1 | 11/2018 | Sawanoi et al. |
| 2019/0053723 | A1 | 2/2019 | van Sparrentak et al. |
| 2019/0150765 | A1 | 5/2019 | Fortin et al. |

FOREIGN PATENT DOCUMENTS

| | | |
|---|---|---|
| CN | 102589760 A | 7/2012 |
| CN | 105828714 A | 8/2016 |
| CN | 105989854 A | 9/2016 |
| DE | 3612532 | 10/1986 |
| DE | 112012005676 T5 | 10/2014 |
| DE | 10 2015 103 261 B3 | 1/2016 |
| EP | 0537383 | 4/1993 |
| JP | H634601 U | 5/1994 |
| JP | H08191779 A | 7/1996 |
| JP | H10295655 A | 11/1998 |
| JP | 2002010984 A | 1/2001 |
| JP | 2003245255 A | 9/2003 |
| JP | 2004305362 A | 11/2004 |
| JP | 2009213767 A | 9/2009 |
| JP | 2009284967 A | 12/2009 |
| JP | 2010284498 A | 12/2010 |
| JP | 2017047093 A | 3/2017 |
| WO | 2009076126 A1 | 6/2009 |
| WO | 2016/040256 A1 | 3/2016 |
| WO | 2016067866 A1 | 5/2016 |
| WO | 2016115035 A1 | 7/2016 |

OTHER PUBLICATIONS

Babbs, C.F., "Oscillometric Measurement of Systolic and Diastolic Blood Pressures Validated in a Physiologic Mathematical Model," BioMedical Engineering OnLine 11:56, Dec. 2012, pp. 1-22.

Baker, P.D., et al., "Theoretical Analysis of Non-Invasive Oscillometric Maximum Amplitude Algorithm for Estimating Mean Blood Pressure," Medical and Biological Engineering and Computing 35(3):271-278, May 1997.

Chen, S., et al., "Assessment of Algorithms for Oscillometric Blood Pressure Measurement," Proceedings of the International Instrumentation and Measurement Technology Conference (I2MTC 2009), Singapore, May 5-7, 2009, 5 pages.

"Continuous Noninvasive Arterial Pressure," Wikipedia, The Free Encyclopedia <https://en.wikipedia.org/wiki/Continuous_noninvasive_arterial_pressure?oldid+675060442>, 6 pages.

(56) References Cited

OTHER PUBLICATIONS

Da Fonseca, L.U.S., et al., "Radial Applanation Tonometry as an Adjuvant Tool in the Noninvasive Arterial Stiffness and Blood Pressure Assessment," World Journal of Cardiovascular Diseases 4(5):225-235, May 2014.

Digiglio, P., et al., "Microflotronic Arterial Tonometry for Continuous Wearable Non-Invasive Hemodynamic Monitoring," Annals of Biomedical Engineering 42(11):2278-2288, Nov. 2014.

Doshi, H., et al., "Does 'Hidden Undercuffing' Occur Among Obese Patients? Effect of Arm Sizes and Other Predictors of the Difference Between Wrist and Upper Arm Blood Pressures," Journal of Clinical Hypertension 12(2):82-88, Feb. 2010.

Drzewiecki, G., et al., "Theory of the Oscillometric Maximum and the Systolic and Diastolic Detection Ratios," Annals of Biomedical Engineering 22(1):88-96, Jan. 1994.

Drzewiecki, G.M., et al., "Arterial Tonometry: Review and Analysis," Journal of Biomechanics 16(2):141-152, 1983.

Forouzanfar, M., et al., "Ratio-Independent Blood Pressure Estimation by Modeling the Oscillometric Waveform Envelope," IEEE Transactions on Instrumentation and Measurement 63(10):2501-2503, Oct. 2014.

"High Blood Pressure," Statistical Fact Sheet, 2014 Update, American Heart Association, 2 pages.

"High Blood Pressure Facts," Centers for Disease Control and Prevention (CDC), Nov. 30, 2016 <https://www.cdc.gov/bloodpressure/facts.htm%5C>, 5 pages.

"Integrated Capacitive Pressure Sensors," Fraunhofer IMS, 2—page brochure.

"Invasive Blood Pressure," @Memscap, Mar. 23, 2018 <http://www.memscap.com/applications-and-market-segments/medical-and-biomedical/invasive-blood-pressure>, 1 page.

Jílek, J., and M. Štork, "The Effect of Wrist Cuff Width on Oscillometric Blood Pressure Waveforms," Electroscope, vol. 2008, No. III, 2008, 4 pages.

Jones, R.D.M., et al., "The Finapres 2300e Finger Cuff: The Influence of Cuff Application on the Accuracy of Blood Pressure Measurement," Anaesthesia 48(7):611-615, Jul. 1993.

Kountz, D.S., et al., "MD Mouse, a New Finger Blood Pressure Monitor, Consistently Underestimates Blood Pressure Compared to a Standard Automatic Syphygnomanometer," Abstract P-54, Journal of the American Society of Hypertension 9(4S):e35-e48, 2015.

Lan, H., et al., "Effect of Tissue Mechanical Properties on Cuff-Based Blood Pressure Measurements," Medical Engineering and Physics 33(10):1287-1292, Dec. 2011.

Lee, J., and K.C. Nam, "Tonometric Vascular Function Assessment," Chap. 30, in Barros de Mello (ed.), "Biomedical Engineering," Intech Europe, Rijeka, Croatia, 2009, pp. 549-566.

Lee, J., et al., "Comparison Between Dynamic Contour Tonometry and Goldmann Applanation Tonometry," Korean Journal of Ophthalmology 23(1):27-31, Mar. 2009.

Lee, J.Y., et al., "Blood Pressure Measurement Using Finger Cuff," Proceedings of the 27th Annual Conference of IEEE Engineering in Medicine and Biology, Shanghai, Sep. 1-4, 2005, 3 pages.

Liu, J., et al., "Patient-Specific Oscillometric Blood Pressure Measurement," IEEE Transactions on Biomedical Engineering 63(6):1220-1228, Jun. 2016.

Lyew, M.A., and J.W. Jamieson, "Blood Pressure Measurement Using Oscillometric Finger Cuffs in Children and Young Adults," Anaesthesia 49(10):895-899, Oct. 1994.

McEniery, C.M., et al., "Central Blood Pressure: Current Evidence and Clinical Importance," European Heart Journal 35(26):1719-1725, Jul. 2014.

Miyashita, H., "Clinical Assessment of Central Blood Pressure," Current Hypertension Reviews 8(2):80-90, May 2012.

Ogedegbe, G., and T. Pickering, "Principles and Techniques of Blood Pressure Measurement," Cardiology Clinic 28(4):571-586, Nov. 2010. (Author Manuscript provided, PMCID:PMC3639494, available in PMC Apr. 30, 2013, 26 pages.).

Pickering, T.G., et al., "Recommendations for Blood Pressure Measurement in Humans and Experimental Animals, Part 1: Blood Pressure Measurement in Humans," Circulation 111(5):697-716, Feb. 2005.

Raamat, R., et al., "Mathematical Modelling of Non-Invasive Oscillometric Finger Mean Blood Pressure Measurement by Maximum Oscillation Criterion," Medical & Biological Engineering & Computing 37(6):784-788, Nov. 1999.

Rosatella, G., et al., "Non Invasive Procedure to Evaluate the Viscoelastic Behavior of the Brachial Artery by Oscillometric Repeated Measurements," Proceedings of the 25th Annual International Conference of the IEEE EMBS, Cancun, Mexico, Sep. 17-21, 2003, pp. 3302-3305.

Schattenkerk, D.W.E., et al., "Nexfin Noninvasive Continuous Blood Pressure Validated Against Riva-Rocci/Korotkoff," American Journal of Hypertension 22(4):378-383, Apr. 2009.

Valentinuzzi, M.E., and A.J. Kohen, "Laplace's Law: What It Is About, Where It Comes From, and How It Is Often Applied in Physiology," IEEE Pulse 2(4):74-84, Jul.-Aug. 2011.

Van Bortel, L.M., et al., "Non-Invasive Assessment of Local Arterial Pulse Pressure: Comparison of Applanation Tonometry and Echo-Tracking," Journal of Hypertension 19(6):1037-1044, Jun. 2001.

Gizdulich, Paolo et al., "Models of Brachial to Finger Pulse Wave Distortion and Pressure Decrement", Cardiovascular Research vol. 33, 1997, pp. 698-705.

Chen, Chen-Huan et al., "Estimation of Central Aortic Pressure Waveform by Mathematical Transformation of Radial Tonometry Pressure", Circulation vol. 95, 1997, pp. 1827-1836.

International Search Report and Written Opinion from the International Searching Authority mailed Apr. 11, 2018, for International Application No. PCT/US2018/012404, filed Jan. 4, 2018, 14 pages.

European Examination Report, mailed Sep. 26, 2022, issued in European Patent Application No. 18704634.7-1113, 7 pages.

Indian Office Action, mailed Feb. 12, 2021, in corresponding Indian Patent Application No. 201947029703, 6 pages.

\* cited by examiner

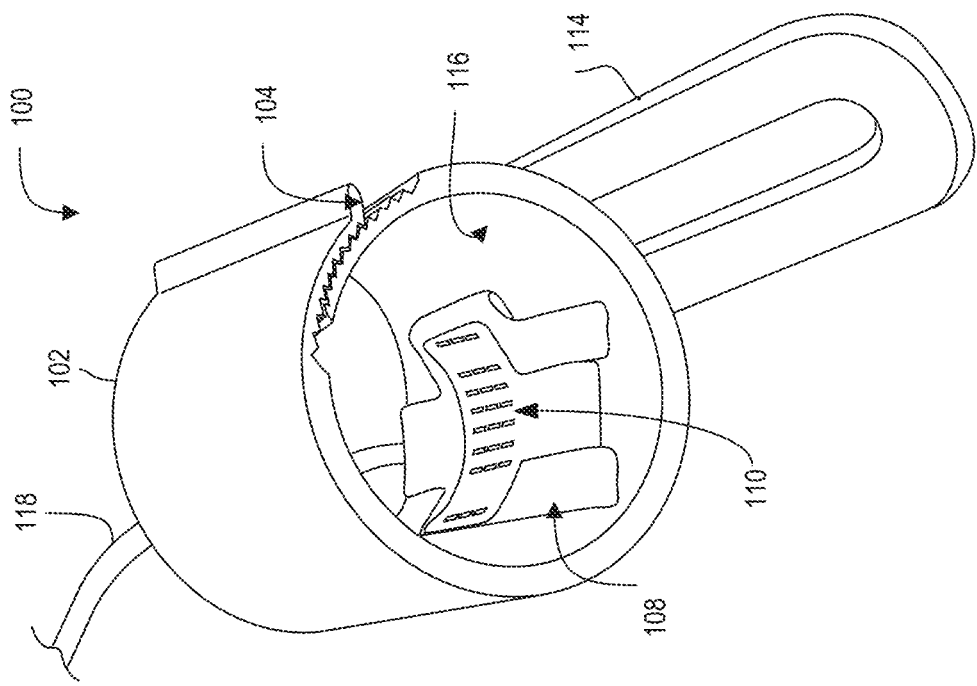
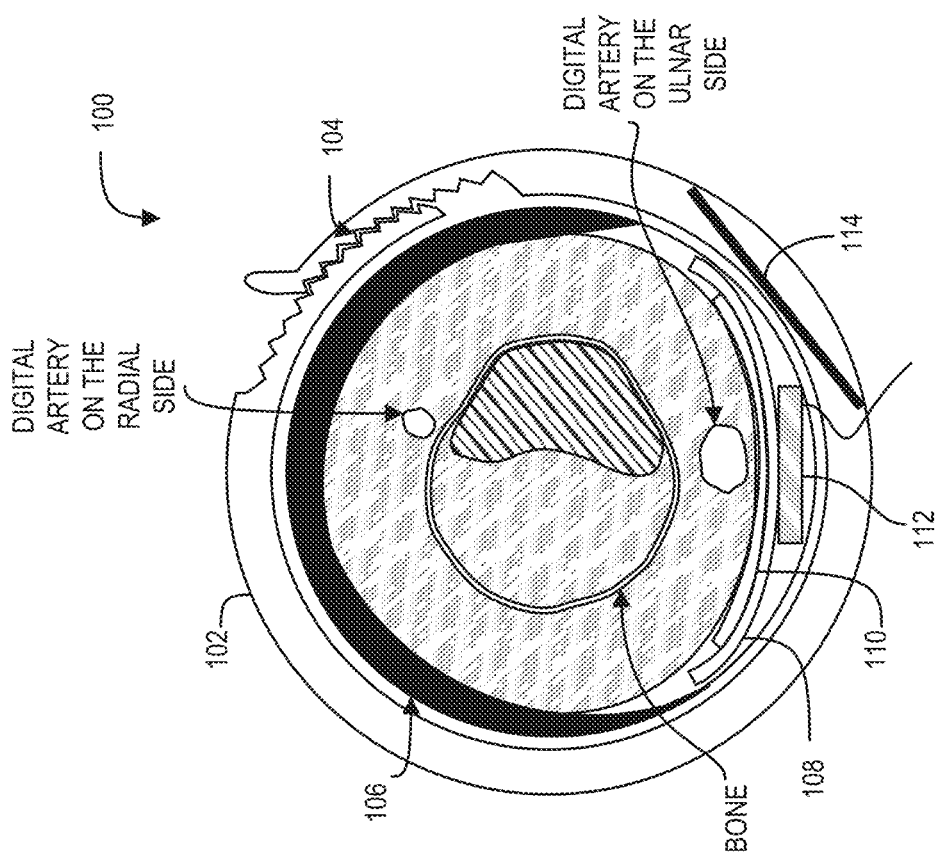

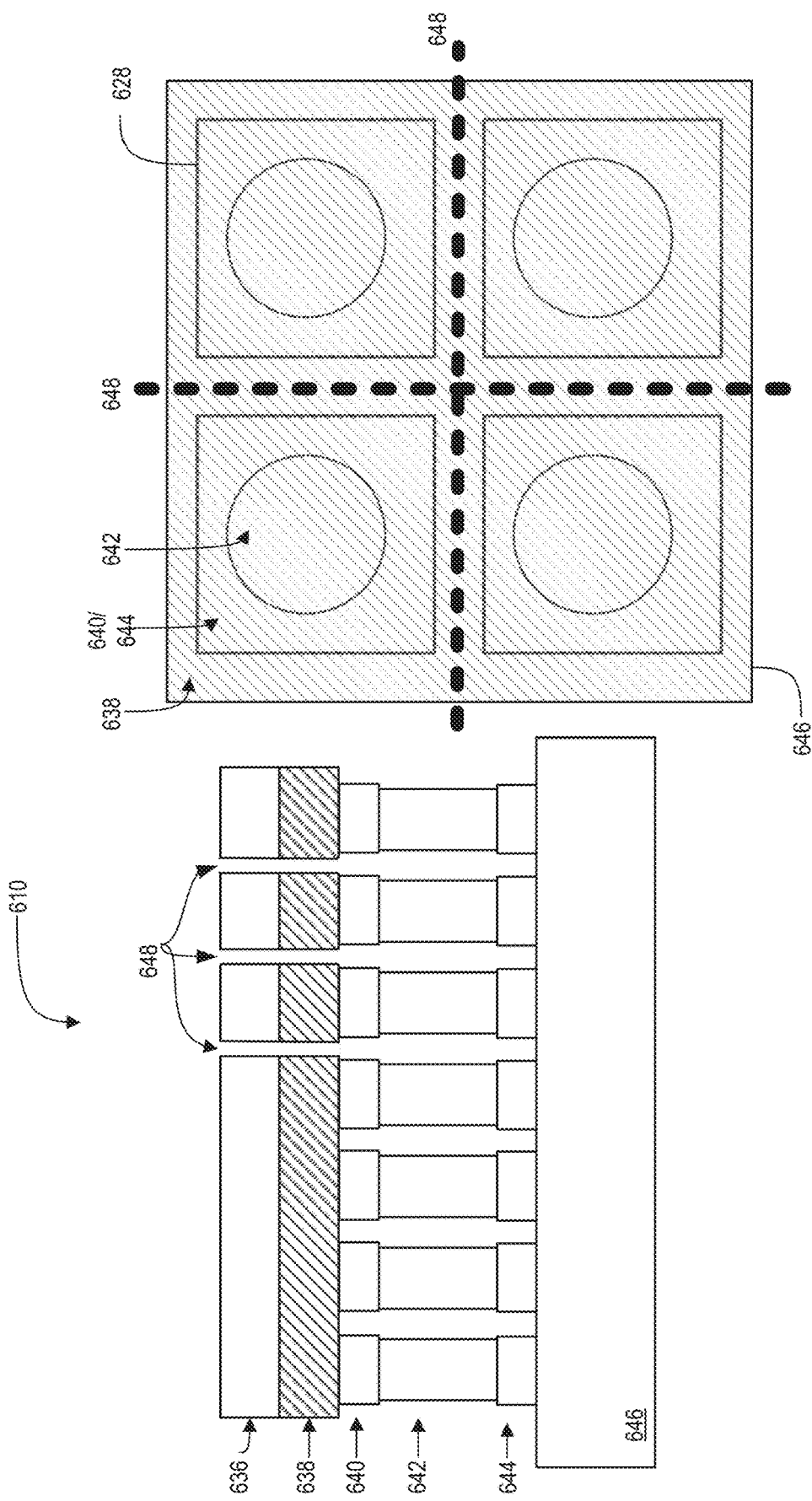

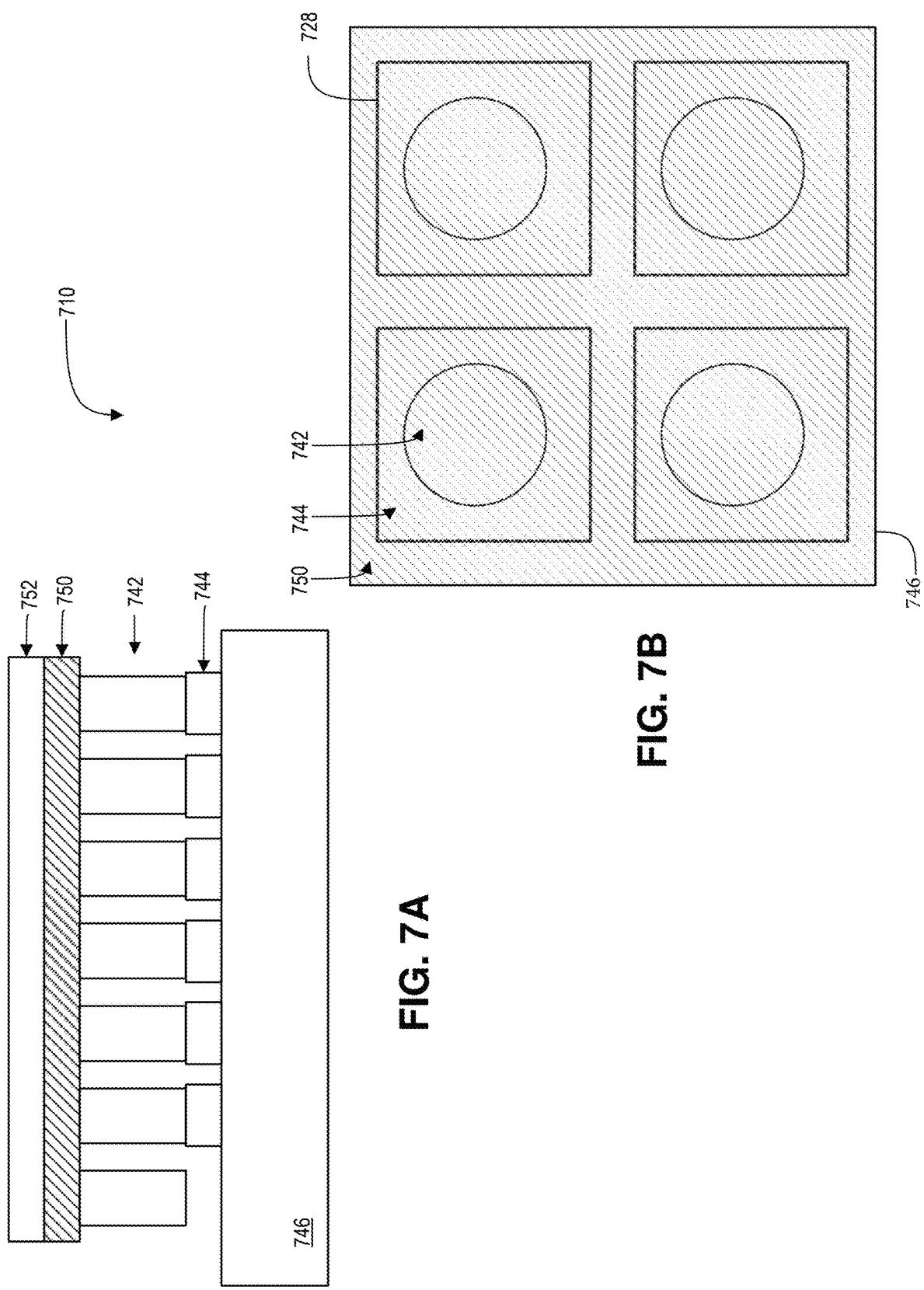

DIGITAL ARTERY BLOOD PRESSURE MONITOR

CROSS-REFERENCE TO RELATED APPLICATION

The present application is a divisional of U.S. application Ser. No. 15/414,354, filed on Jan. 24, 2017, the contents of which are hereby incorporated by reference.

TECHNICAL FIELD

This disclosure relates generally to blood pressure monitoring, and in particular but not exclusively, relates to blood pressure monitoring at a digital artery.

BACKGROUND INFORMATION

High blood pressure is a health concern for a large percentage of the population, but regular monitoring is not common place. Blood pressure monitors have conventionally been mainly used at a physician's office, hospital, and/or the occasional automated system found in pharmacies, but are not frequently used by those who suffer high blood pressure outside of the occasional office visit or while waiting for a prescription at the pharmacy. Additional monitoring of blood pressure is requested by many physicians, but patients rarely follow through due to difficulty in obtaining readings, expense of portable units, or they avoid the readings due to the associated discomfort. The associated discomfort typically due to the squeezing of the arm or wrist, for example. As such, it may be desirable to have portable, easy to use, and less painful blood pressure monitoring devices.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIG. 1A is a blood pressure monitoring device 100 in accordance with an embodiment of the present disclosure.

FIG. 1B is a perspective view of the finger wearable blood pressure monitoring device 100 in accordance with an embodiment of the present disclosure.

FIGS. 6A and 6B are a cross-sectional view and a plan view, respectively, of a tactile sensor array (TSA) 610 in accordance with an embodiment of the present disclosure.

FIGS. 7A and 7B are a cross-sectional view and a plan view, respectively, of a TSA 710 in accordance with an embodiment of the present disclosure.

DETAILED DESCRIPTION

Figure 2:
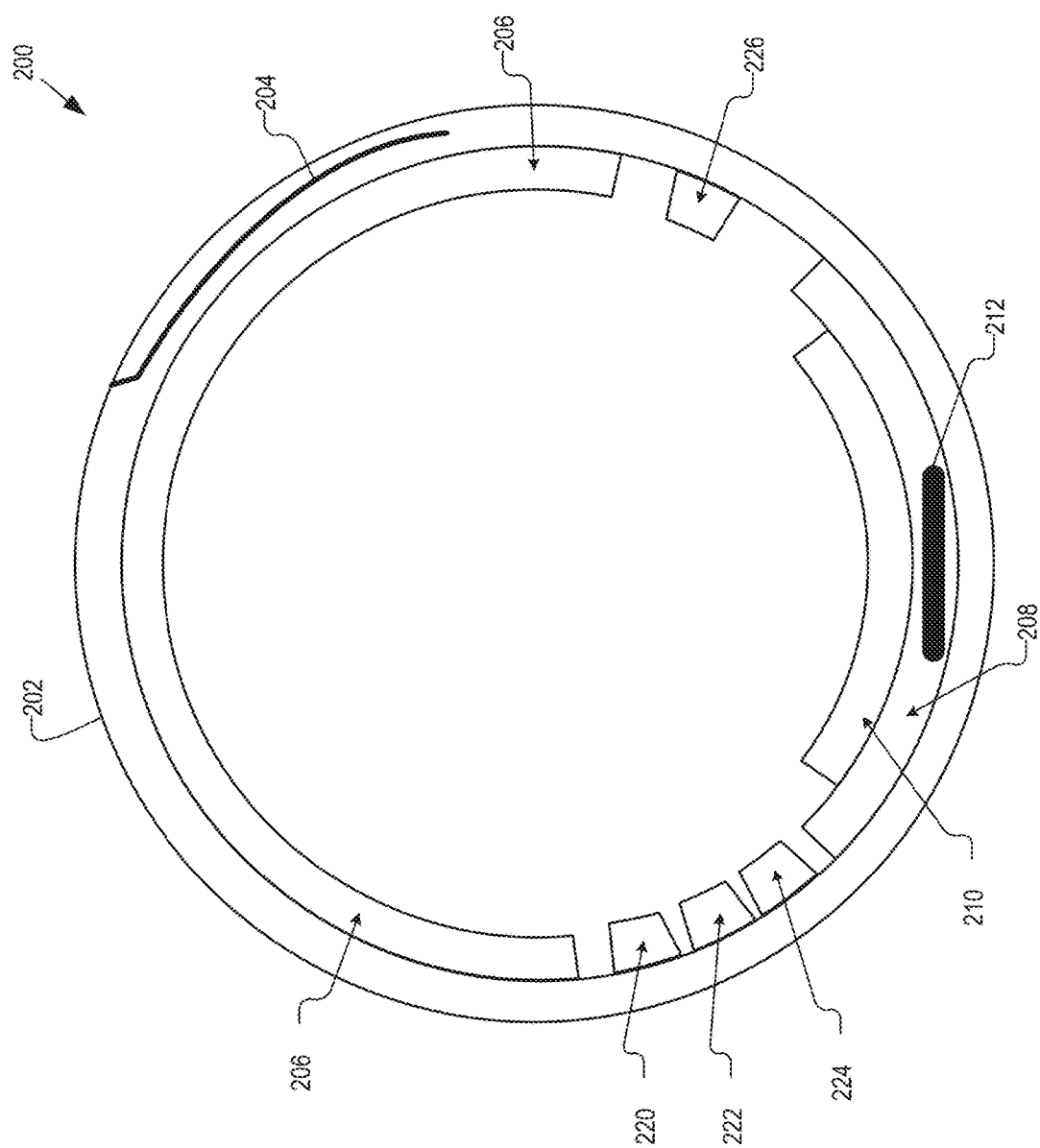
FIG. 2 is a finger wearable blood pressure monitoring device 200 in accordance with an embodiment of the present disclosure.

Embodiments of a system and method for measuring blood pressure at a digital artery are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Hypertension, e.g., high blood pressure, may affect large numbers of the population, but the extent may be uncertain due to gaps in blood pressure data. For example, outside of individuals who see a physician regularly for various health concerns, most adults may only have their blood pressure read once, maybe twice, a year. Further, variability in blood pressure over time or throughout the day may be a diagnostic indicator of other ailments that may not be apparent to the individual. As such, more blood pressure readings at various times of the day and year may be desirable to help physicians better understand their patient's holistic health.

Although there are blood pressure monitoring stations at some pharmacies, and blood pressure monitoring devices available for purchase, adoption of these means and devices may be lacking. The lack of adoption may be due to costs of the devices or unwanted trips to the pharmacy. However, even those individuals who do some self blood pressure monitoring may take readings less often than desirable because the methods/devices are either cumbersome to operate, painful, or a combination thereof. Additionally, the data individuals may obtain on their own likely never gets communicated to their physician. Moreover, monitoring of blood pressure by individuals may be undesirable for several additional reasons, such as complacency by the individuals, the pain associated with the blood pressure monitoring, lack of transportation, etc.

As such, it may be desirable to have a portable, compact device that may less intrusively monitor a user's blood pressure. It may be further desirable for the device to be small, simple to operate, and be capable of reporting blood pressure readings to a physician or a patient's electronic medical records.

One way to provide for blood pressure monitoring may be a finger-wearable device that monitors blood pressure in a digital artery, such as the digital artery on the ulnar or radial sides for example. The finger-wearable device may use oscillometry, auscultation, or applanation tonometry to estimate a user's blood pressure at the digital artery, which may subsequently be converted to a clinical or brachial blood pressure. For applanation tonometry, the finger-wearable device may include a tactile sensor array that may be pressed into the finger over the digital artery, which may deform to digital artery. The digital artery may or may not be deformed to occlusion. As the pressure of the finger onto the tactile sensor array is slowly reduced, the digital artery may slowly convert back to a normal shape, and may pass through a point where the internal pressure equals the external pressure exerted on the digital artery by the TSA. This point may occur when a local radius of the digital artery approaches infinity, e.g., zero, at least in reference to a size of a capacitive sensor of the tactile sensor array. In this state, e.g., with the local radius of curvature of the digital artery flat, the blood flow in the artery due to heart beats may cause the flat area of the digital artery to experience fluctuations. A maximum fluctuation may occur at the flat condition, and increases/decreases of the fluctuations may occur when the local radius is not quite flat. While the above operation was discussed in terms of a controlled reduction in pressure between the finger and the tactile sensor array, the operation may alternatively be performed using a controlled increase in pressure and the capacitance changes may be measured during the controlled increase.

The tactile sensor array may include deformable capacitive sensors that may be deformed due to the fluctuations in the arterial wall. These fluctuations may change a shape, e.g., height, of one or more deformable capacitive sensors, which may change their capacitance values. The changing capacitance may be measured, which provides an indication of the blood pressure in the digital artery. The capacitance levels of the capacitive sensors may be converted into pressure levels, e.g., mmHg. A maximum amplitude of the capacitance fluctuations/changes may be an estimate of a mean arterial pressure at the digital artery. Then, a systolic and a diastolic blood pressure at the digital artery may be estimated based on the mean arterial pressure. Subsequently, the digital artery blood pressure estimates may be converted to clinical or brachial blood pressure measurements.

To implement auscultation, the digital artery may be pressed to occlusion by the finger-wearable device then the pressure slowly reduced. A microphone included in the device may record sounds, known as Korotkoff sounds, originating in the digital artery as the blood begins to flow. The Korotkoff sounds change in character as the pressure applied to the artery is decreased. The applied pressure corresponding to the first Korotkoff sound may be an estimate of the systolic blood pressure, and the applied pressure corresponding to the termination of the Korotkoff sounds may be an estimate of the diastolic blood pressure.

To implement oscillometry, the digital artery may be pressed or squeezed by a bladder to a pressure at least above the systolic blood pressure, then the pressure may be slowly reduced. During the reduction in pressure, an air pressure sensor measuring the pressure in the bladder may also measure pressure oscillations in the bladder due to blood flow in the digital artery. The pressure oscillations may start small, increase to a maximum amplitude, and reduce. Similar to the applanation tonometry technique, the applied pressure at maximum amplitude may be an estimate of the mean arterial pressure. From the mean arterial pressure, a systolic and diastolic pressure may be estimated.

FIG. 1A is a blood pressure monitoring device 100 in accordance with an embodiment of the present disclosure. The blood pressure monitoring device 100, device 100 for short, may be worn or engaged with a digital artery, e.g., a finger, to determine the blood pressure of a user, along with other diagnostic data. In some embodiments, the other diagnostic data may include heart rate (HR), respiratory rate (RR), temperature, and blood oxygen saturation (SpO2). In some embodiments, motion of the device 100 may also be detected. The device 100 may be worn on a finger of a user throughout the day, night, both, or periodically to monitor the user's blood pressure. In some embodiments, the device 100 may provide blood pressure readings, and the other diagnostic data/movement data to an external reader (not shown). In turn, the external reader may record the data, alert the user and/or user's physician to readings outside of designated ranges, or transmit the data to an electronic medical record associated with the user, for example.

The illustrated embodiment of the device 100 includes a cuff 102, a size adjustment mechanism 104, a bladder 106, a substrate 108, a tactile sensor array (TSA) 110, control circuitry 112, and an alignment tab 114. The device 100 may be worn on a finger with the TSA 110 oriented to align with a digital artery of the finger. In some embodiments, the TSA 110 may be aligned 45° to the palm so that the TSA 110 is centered over the digital artery on the ulnar side of the finger. The size adjustment mechanism 104 may be adjusted to ensure a snug fit around the finger. In some embodiments, the bladder 106 may be dynamically inflated to ensure that the digital artery and the TSA 110 are pressed together. Subsequently, the TSA 110 may measure blood pulses in the digital artery, which may be converted into mean arterial pressure (MAP), systolic blood pressure (SBP), and/or diastolic blood pressure (DBP). In some embodiments, the control circuitry 112 may perform the conversion. In other embodiments, the measurements may be transmitted, via wire or wirelessly, to an external reader for the conversion process. While the device 100 includes the bladder 106 to facilitate pressure of the finger to the TSA 110, in other embodiments, the bladder may be omitted and the size adjustment mechanism 104 may be adjusted to provide the necessary pressure.

The cuff 102 may be formed to fit at least partially around a finger and may further provide support for the various other components. The cuff 102 may be formed from plastic, metal, ceramic, or any biocompatible material not likely to affect the BP monitoring components/measurements. The cuff 102 may be ring-shaped with a radial thickness, a width (along the finger), and a circumference/diameter. The radial thickness may be thick enough to provide non-deformable support to the bladder 106 and TSA 110. The circumference may range from 22 to 25 mm, but may also be adjustable by the size adjustment mechanism 104 to fit a wide range of finger sizes. For example, the cuff 102 may be adjustable to fit around an index finger or a pinky finger. In some embodiments, the width and circumference of the cuff 102, especially an inner surface of the cuff 102, may be based on guidelines set by the AHA (American Heart Association) regarding inflatable cuff dimensions with respect to an arm circumference. Per the guidelines, the bladder 106 should have a length that is 80% and a width that is 40% of an arm circumference, which results in a length-width ratio of 2:1. As such, the inner circumference of the cuff 102 may desirably be large enough to allow the circumference and width of the bladder 106 to satisfy the ratio in regards to a finger circumference.

The size adjustment mechanism 104 may be incorporated into a portion of the cuff 102, and may allow a user to adjust the size, e.g., circumference, of the cuff 102 to obtain a desired fit. In some embodiments, the desired fit may be a snug fit that allows the finger and the TSA 110 to be in intimate contact. It may be desirable to prevent a loose fit of the device 100 on the finger. However, the device 100 may operate as intended even when loosely worn on a finger due to the bladder 106 pressing the finger against the TSA 110. In some embodiments, the size adjustment mechanism 104 may be a ratcheting-type adjustment as shown in FIG. 1. In other embodiments, the size adjustment mechanism 104 may be formed from hook and loop, buckle, etc. types of mechanisms. Of course, the size adjustment mechanism 104 may be omitted and the cuff 102 may be fitted or may be available in various sizes depending on the user's fingers.

The bladder 106 may be disposed on an inner surface of the cuff 102 and, in some embodiments, may be disposed along a majority of the inner circumference of the cuff 102. In some embodiments, the bladder 106 may generally be disposed on an inner surface opposite from the location of the TSA 110. The bladder 106 may be formed from a soft, flexible material that may enlarge/stretch due to an increase in internal pressure. In some embodiments, air may be introduced, e.g., pumped, in the bladder 106 to cause the bladder 106 to expand. In other embodiments, a refrigerant coupled to or disposed within the bladder 106 may undergo a phase transition from liquid to gas to provide the desired expansion, with the phase transition induced through heating the refrigerant. Alternatively, the bladder 106 may be replaced by a shape memory alloy that may press the finger into the TSA 110 in response to a control voltage, for example, or a mechanical actuator may be used to press the finger onto the TSA 110. Although not shown in FIG. 1, a pressure sensor may be disposed within the bladder 106 to measure the internal pressure of the bladder 106. In some embodiments, the pressure sensor may be used to implement oscillometric estimates of the blood pressure. Expansion of the bladder 106 may force a user's finger to be pressed more tightly against the TSA 110, which may provide better interaction between the TSA 110 and the digital artery aligned with the TSA 110.

The substrate 108 may provide a mounting surface for the TSA 110 and/or the control circuitry 112. The substrate may be formed from a rigid material, such as plastic, ceramic, or metal, and may be disposed on the inner surface of the cuff 102.

The TSA 110 may be a sensor array formed from a plurality of individual capacitive sensors. The TSA 110 may be disposed on the substrate 108 and arranged to be in contact with the finger of the user. The plurality of capacitive sensors may be arranged into a two-dimensional array comprising a number of columns and a number of rows. In some embodiments, the columns may be arranged to align longitudinally with the finger and the rows align circumferentially. Of course, the opposite arrangement of the columns and rows may be implemented. In some embodiments, there may be more columns than rows to ensure the TSA 110, or at least a column of capacitive sensors, is centered over the digital artery area of the finger. In general, it may be desirable to have at least one capacitive sensor of the TSA 110 to contact the skin directly above the digital artery so that pressure changed in the digital artery may be measured as changes in capacitance of the at least one capacitive sensor. Additionally, the TSA 110 may be formed from a soft, flexible material that conforms the inside shape of the cuff 102 and/or fits at least partially around the finger. Alternatively, the TSA 110 may have a semi-circumferential shape to at least conform to an outside of the finger.

In some embodiments, the TSA 110 may include a Kapton® or Polyimide capsulant layer on the finger side of the TSA 100. The Kapton® or Polyimide layer may provide a mechanical, protective layer to the TSA 110. In some embodiments, however, the Kapton® or Polyimide layer may be separated between the rows, columns, or individual capacitive sensors to mechanically decouple adjacent rows, columns, or individual capacitive sensors. In other embodiments, the TSA 110 may include a conductive cloth layer that provides an electrode to the individual capacitive sensors. The conductive cloth may mechanically decouple adjacent capacitive sensors of the TSA 110. In general, the TSA 110 may be coupled to detect and measure blood flow in the digital artery due to heart beats, and the resulting blood pressure. For example, one or more individual capacitive sensors of the TSA 110 may be aligned with the digital artery and may detect changes pressure changes within the digital artery due to the capacitive sensor deforming in response to pressure changes within the digital artery, which indicate blood flow and blood pressure. The detected changes in pressure, which cause a change in the capacitance reading of the TSA 110, may be converted into MAP at the digital artery, which may subsequently be converted into SBP and DBP at the digital artery.

The control circuitry 112 may be coupled to choreograph the operation of the device 100, and may be disposed between the inner surface of the cuff 102 and the substrate 108. In some embodiments, the control circuitry 112 may be disposed on a side of the substrate 108 facing the inner surface of the cuff 102. In other embodiments, the control circuitry 112 may be disposed on the inner surface of the cuff 102 underneath the substrate 108. The control circuitry 112 may be coupled to the TSA 110 to receive capacitance readings, and may be further coupled to the bladder 106 to control inflating and deflating. Additionally, the control circuitry 112 may be coupled via a wire or wirelessly to an external reader for providing and receiving data and/or power.

The alignment tab 114 may assist the user in aligning the TSA 110 to a desired digital artery. For example, the alignment tab 114 may be aligned with the palm so that the TSA 110 may be aligned with the digital artery. In some embodiments, the TSA 110 may be aligned with the digital artery on the ulnar side of the finger, and the alignment may be facilitated by the alignment tab 114. While the digital artery on the radial side of the index finger may also be used to monitor BP, the digital artery on the ulnar side may be more desirable due to it being larger and closer to the skin surface than the digital artery on the radial side. It is also possible to measure the BP from other fingers, including the long finger, ring finger and little finger.

FIG. 1B is a perspective view of the finger wearable blood pressure monitoring device 100 in accordance with an embodiment of the present disclosure. FIG. 1B shows the TSA 110 disposed on the substrate 108, which is disposed on an inner surface 116 of the cuff 102. An electrical connection 118 may be coupled to the control electronics 112 (not shown), which may be disposed beneath the substrate 108. Additionally, the alignment tab 114 is shown to be a long extension coupled to the cuff 102. The long extension may be slid into or positioned in/on the palm of a user when a user puts the device 100 on a finger. In the shown orientation of the TSA 110 to the alignment tab 114, the device 100 may be worn on a left hand so that the TSA 110 is aligned with the digital artery on the ulnar side, for example. Although the alignment tab 114 is shown to be extending form the cuff 102, in other embodiments, alignment may be assisted from markings placed on the cuff 102.

In operation, the device 100 may detect and monitor the user's BP, along with the various other diagnostic variables. In some embodiments, the device 100 may implement applanation tonometry to determine the user BP at the digital artery, which may then be transformed into a brachial BP measurement. In other embodiments, the device 100 may implement oscillometry and/or auscultation to monitor the BP in the digital artery. In general, the bladder 106 may be inflated to cause the finger to press onto the TSA 110, then the bladder 106 may be deflated. During either the inflation or the deflation of the bladder 106, the TSA 110 may measure pressure pulses in the digital artery that may be converted into blood pressure estimations. For example, the bladder 106 may be inflated in a slow, controlled manner, and the pressure pulses may be measured when the TSA 110 is being slowly pressed into the digital artery. Alternatively or additionally, the pressure pulses may be measured during a slow, controlled deflation of the bladder 106, which may allow the TSA 110 to slowly decrease pressure applied to the digital artery. In either operation, the TSA 110 may create a condition on the arterial wall of the digital artery that allows applanation tonometry to be performed, e.g., when a local radius of curvature of the digital artery approaches infinity, at least compared to a size of a capacitive sensor of the TSA 110. While the detailed operation of the device 100 may be described in terms of deflation of the bladder 106, the same principles of operation may be applied during a slow, controlled inflation of the bladder 106.

To determine the BP using applanation tonometry, such as a MAP that can be used to determine SBP and DBP, the control circuitry 112 may cause the bladder 106 to inflate to a pressure that is at least above the SBP of the user. In some embodiments, the bladder 106 may be inflated until occlusion of the digital artery. Inflating to occlusion, however, may not be necessary, but may be performed when the device 100 is initially used to ensure the pressure is above SBP. To determine if occlusion is reached, the TSA 110 may monitor for pressure changes via capacitance measurements. Once the bladder 106 has been inflated to the desired pressure, the control circuitry 112 may deflate the bladder 106 at a slow and controlled rate. For example, the bladder 106 may be deflate at a rate of 2 to 3 mmHg per second. While the bladder is deflating, the TSA 110 may measure pressure changes occurring within the digital artery due to the BP and blood flow. As the pressure exerted by the bladder 106 decreases, the external pressure on the digital artery will decrease. The decrease in the external pressure on the digital artery affects the differential between the external pressure on the artery and the internal pressure on the artery. As these two pressures tend toward being equal, at which time the arterial wall may be flat at least in regards to the capacitive sensor of the TSA 110, the blood flow pulses due to the heart beat begin to show a change as detected by the TSA 110. The changes may appear as pulsatile waveforms or fluctuations in the capacitive measurements/levels of the TSA 110. The pressure at which a maximum amplitude occurs in a pulsatile waveform may be the MAP (mean arterial pressure), which may be indicative of the user's BP in the digital artery. After detection of MAP, the control circuitry 112 may provide the data to an external reader for algorithmic manipulation to extract SBP and DBP from the MAP, or the control circuitry 112 may estimate the MAP, SBP and DBP.

In response to the determination of MAP, SBP and/or DBP, the device 100 may perform various tasks. For example, if the BP data show a high BP reading, the user may be alerted via the external reader to consult their physician or remind the user to take their BP medication. Alternatively, the data may be provided by the device 100 to be logged on the external reader, which may periodically upload the data to the user's electronic medical records, or to an application, for example. In some embodiments, the external reader may provide distractions to the user while a BP reading is performed. For example, the external reader, which may be a smartphone, may provide news, weather, games, or heart beat waveforms while a BP reading is performed.

While the device 100 may be a ring-type device to be freely worn on a finger, the device 100 may be included in various other wearable or handheld devices as well. For example, the device 100 may be inserted into a finger of a glove to be worn by the user, or the device 100 may be included in a handheld device that may include a display and other indicators to assist the user with operation.

FIG. 2 is a finger wearable blood pressure monitoring device 200 in accordance with an embodiment of the present disclosure. The finger wearable blood pressure monitoring device 200, device 200 for short, may be an example of the device 100. The device 200 may be formed to fit, at least partially, around a finger to monitor for blood pressure and other diagnostic data using a digital artery. For example, the device 200 may detect a digital artery-based BP using one or more capacitive sensors, and augment the BP data with heart rate, respiratory rate, temperature, sound, and movement data. The other diagnostic data may provide information to a user or physician on their own, but may also be used to inform the BP measurement. In general, the device 200 may determine a MAP at the digital artery, which may then be algorithmically converted into SBP and DBP at the digital artery. Additionally, the digital artery BP data may be converted to clinical/brachial BP data through one or more transfer functions. In some embodiments, estimation of the BP at the digital artery and/or the conversion to the clinical/brachial BP may be performed by control logic included in the device 200. In other embodiments, the control circuitry may provide the raw capacitance data along with other sensor data to an external device for analysis and reporting of the data and BP estimation.

The illustrated embodiment of the device 200 includes a cuff 202, a size adjustment mechanism 204, a bladder 206, a substrate 208, TSA 210, control circuitry 212, accelerometer 220, temperature sensor 222, photoplethysmography (PPG) sensor 224, and a microphone 226. The cuff 202, size adjustment mechanism 204, bladder 206, substrate 208, and TSA 210 may be analogous to like components of the device 100, and, as such, a detailed discussion with respect to FIG. 2 is omitted for sake of brevity.

The accelerometer 220 may measure movement of the finger and provide the measurements to the control circuitry 212. The accelerometer 220 may be disposed on the cuff 202, such as an inner surface of the cuff, or may be imbedded into the cuff 202. Movement of the finger during a BP measurement may affect the accuracy of the measurement. However, with knowledge of the intensity of the movement, the control circuitry 212 may ignore the movement and continue the reading, halt the reading, adjust the reading based on the movement, or reject the BP reading. Additionally, the accelerometer may be used to reduce hydrostatic effects of the BP reading that occur when the finger is at a different elevation/height than the heart. For example, the accelerometer may measure movement and orientation of the device 200 before a BP reading if the user is prompted to move the finger level with their heart.

The temperature sensor 222 may be disposed on the inner surface of the cuff 202 and be arranged to be in intimate contact with the finger at least during a BP reading. The temperature sensor 222 may measure a temperature of the finger, such as skin temperature, and provide the measurement to the control circuitry 212. The temperature measurement may be used to adjust for vasomotor effects in the digital arteries. Because digital arteries are more susceptible to vasoconstriction and vasodilation, which may alter the peripheral blood flow and BP measurements, the temperature of the finger may be used to compensate the BP measurement if the temperature is outside of a set range. For example, if the temperature is less than 25 Celsius or greater than 40 Celsius, the BP estimation may be adjusted. For example, if the finger temperature is low, the device may request the user to warm the hands and repeat a measurement. Alternatively, the device may use the changes in compliance of the digital artery at different temperatures to correct the raw BP estimates.

The PPG sensor 224 may be disposed on the inner surface of the cuff 202 and be arranged to emit light through the finger and detect the light as it propagates out of the finger. The PPG sensor 224 may include red and/or infrared emitters and respective receivers/detectors, for example. The red and infrared emitters may be light emitting diodes (LEDs) and the receivers, which may be tuned to red and infrared wavelengths, may be photodetectors. The PPG sensor 224 may be used to detect heart rate (HR), respiratory rate (RR), and blood oxygen saturation (SpO2) of the user based on absorption of the red and infrared light. Additionally, the PPG sensors 224 may be used to detect timing of the pulses occurring in the digital artery. The timing information may be used to inform when to begin and/or to end the BP measurements, for example. The light absorption data determined by the PPG sensor 224 may be provided to the control circuitry 212, which may then determine the HR, RR and SpO2 based thereon.

The microphone 226 may also be disposed on the inner surface of the cuff 202, and be coupled to record the blood pulses occurring in the digital artery. In some embodiments, the microphone 226 may be a piezoelectric microphone. The sound recordings, which may be provided to the control circuitry 212, may be used to detect Korotkoff sounds for blood pressure estimation. The Korotkoff sounds may be used to implement auscultatory techniques.

The control circuitry 212 is coupled to the various sensors and electronic components of the device 200, and choreographs the operation of the device. The control circuitry 212 may include an analog-to-digital converter (ADC) coupled to receive the analog signals from the various sensors and convert the same into digital representations. The digital representations may then be used by the control circuitry 212 to determine the user's digital BP and provide the HR, RR and SpO2 as well. Else, the control circuitry 212 may provide the digital representations via a wired or wireless connection to an external reader for determination of the digital artery BP. In some embodiments, the control circuitry 212 may receive capacitance measurements from the TSA 210, which may then be used to determine the MAP, and in turn the SBP and DBP of the user. Else, the capacitive measurements may be provided to the external reader for estimation of the MAP, SBP and DBP.

Figure 3:
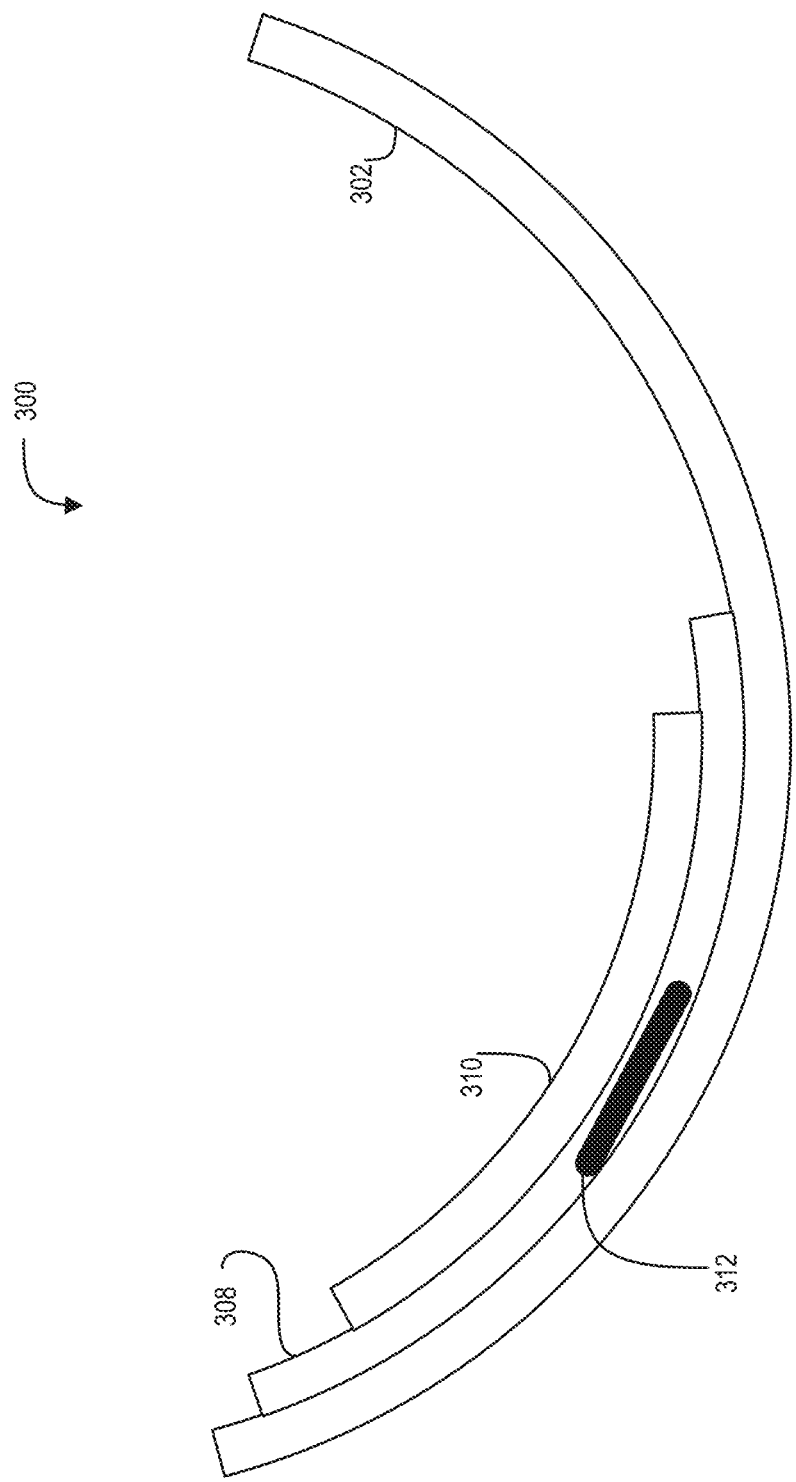
FIG. 3 is a finger-based blood pressure monitoring device 400 in accordance with an embodiment of the present disclosure.

FIG. 3 is a finger-based blood pressure monitoring device 300 in accordance with an embodiment of the present disclosure. The finger-based blood pressure monitoring device 300, device 300 for short, may be an example implementation of the device 100 and/or 200. The device 300 may be mounted to a stationary surface, contained within a glove, or included in a handheld device, for example, that allows a user to place a finger into the device 300 for measurement of the user's BP. The illustrated embodiment of the device 300 includes an immobilizer 302, a substrate 308, and a TSA 310. The other features of devices 100 and/or 200 that are not shown in FIG. 3 may also be included, but have been omitted for sake of brevity.

The immobilizer 302, which may be a cuff that does not fully wrap around a user's finger, may be mounted to stable surface, such as a desk, counter, sink, included in a finger of a glove, or part of a handheld device. The substrate 308 and the TSA 310 may be mounted on an inner surface of the immobilizer 302. In some embodiments, at least the TSA 310 may be mounted offset from a bottom of the immobilizer 302 so that it may be aligned to a digital artery, such as the ulnar artery.

In operation, a user may place a finger into the device 400 so that the TSA 310 is aligned correctly. The immobilizer 302 may include markings to inform the user the desired finger placement to achieve the desired arterial alignment. Upon pressing onto the device 400, the TSA 310 may begin to measure capacitive changes in the TSA 310 to estimate digital BP of the user. In some embodiments, the device 400 may include one or more indicators (not shown), such as LEDs, to indicate to the user if enough pressure is being applied, whether correct alignment has been obtained, and when the reading is complete.

Figure 4:
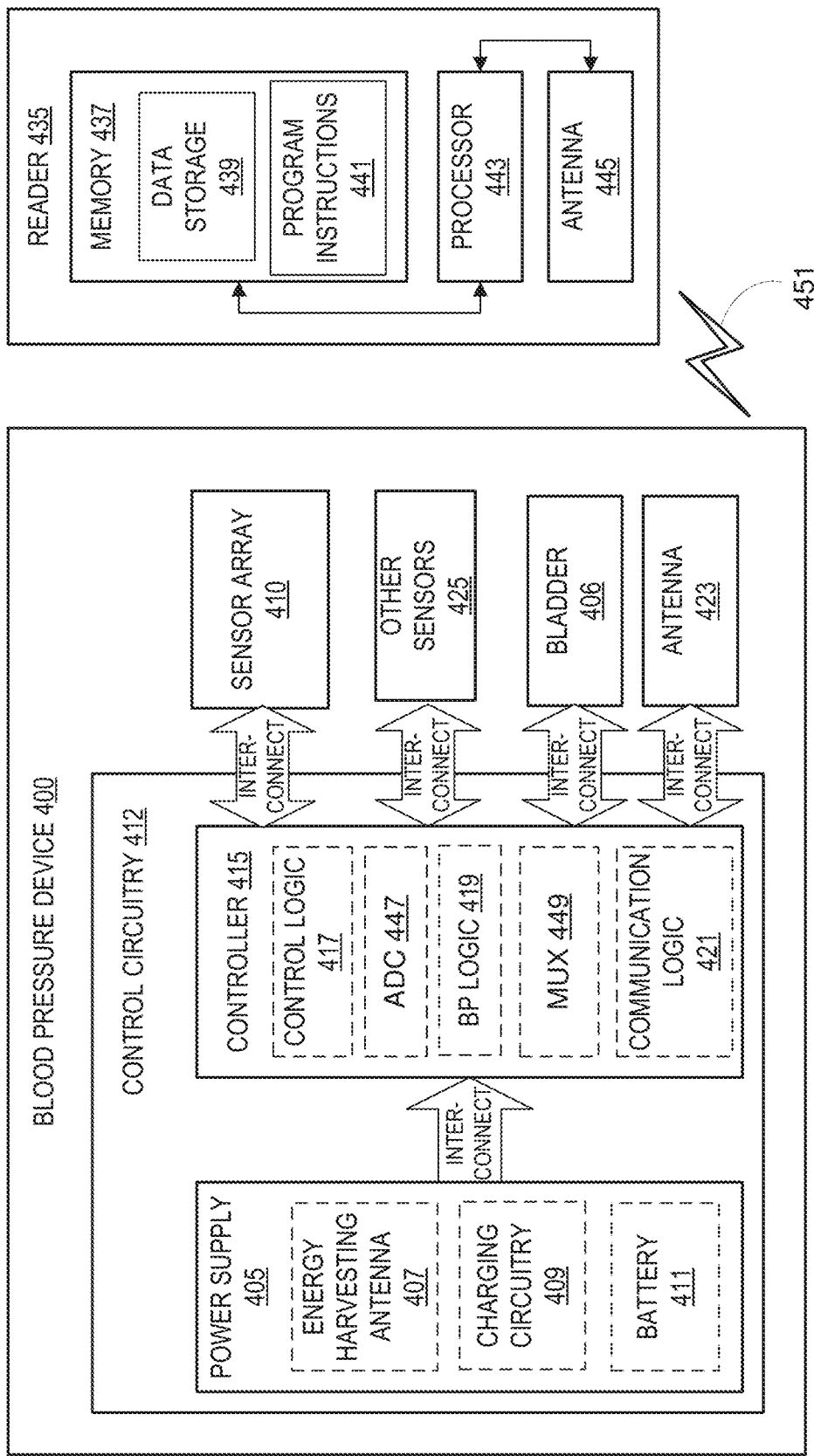
FIG. 4 is a functional block diagram of a finger-wearable BP monitoring device 400 in accordance with an embodiment of the present disclosure.

FIG. 4 is a functional block diagram of a finger-wearable BP monitoring device 400 in accordance with an embodiment of the present disclosure. The device 400 may be an example of the devices 100, 200, and/or 300. In the depicted embodiment, device 400 includes control circuitry 412. The control circuitry 412 may be one implementation of the control circuitry 112, 212 and/or 312. The illustrated embodiment of the control circuitry 412 includes a power supply 405 and a controller 415. The illustrated embodiment of power supply 405 includes an energy harvesting antenna 407, charging circuitry 409, and a battery 411. The illustrated embodiment of controller 415 includes control logic 417, BP logic 419, ADC 447, multiplexer 449, and communication logic 421.

Power supply 405 supplies operating voltages to the controller 415 and various other sensors and components of the device 400. Antenna 423 is operated by the controller 415 to communicate information to and/or from device 400. In the illustrated embodiment, antenna 423, controller 415, and power supply 405 are disposed on substrate, such as the substrate 108.

In the illustrated embodiment, power supply 405 includes a battery 411 to power the various embedded electronics, including controller 415. Battery 411 may be inductively charged by charging circuitry 409 and energy harvesting antenna 407. In one embodiment, antenna 423 and energy harvesting antenna 407 are independent antennae, which serve their respective functions of energy harvesting and communications. In another embodiment, energy harvesting antenna 407 and antenna 423 are the same physical antenna that are time shared for their respective functions of inductive charging and wireless communications with reader 435. In yet other embodiments, the battery 411 may be charged via a wire plugged into the device 400.

Charging circuitry 409 may include a rectifier/regulator to condition the captured energy for charging battery 411 or directly power controller 415 without battery 411. Charging circuitry 409 may also include one or more energy storage devices to mitigate high frequency variations in energy harvesting antenna 407. For example, one or more energy storage devices (e.g., a capacitor, an inductor, etc.) can be connected to function as a low-pass filter.

Controller 415 contains logic to choreograph the operation of the other embedded components. Control logic 417 controls the general operation of device 400, including providing a logical user interface, power control functionality, etc. Additionally, control logic 417 controls the inflation and deflation of the bladder 406 and receives pressure data from a pressure sensor included in the bladder 406. Analog to digital converter (ADC) 447 may receive data from the other sensors 425 and the sensor array 410. The ADC 447 may convert the received data to a digital format and provide the same to the control logic 417 and/or the BP logic 419. In some embodiments, the ADC 447 may be coupled to the sensor array 410 and the other sensors 425 via the MUX 449, which controls the inflow of data to the ADC 447.

The BP logic 419 may receive the capacitance measurements form the sensor array 410 and convert the capacitance measurements into equivalent pressure values. The pressure values may be in mmHg, for example. The pressure values may further be converted into pressure waves that may be analyzed in either the time or frequency domains to determine MAP, SBP and DBP at the digital artery. In some embodiments, the blood pressure data at the digital artery may be transformed to corresponding blood pressure data at the brachial location, for example. The pulse waves may be analyzed by the BP logic 419 to determine a pressure at which a maximum pulsatile amplitude occurs. The determined pressure may be based on one capacitive sensor of the sensor array 410, on an average of all the capacitive sensors, or based on a lowest determined pressure.

In some embodiments, the BP logic 419 may receive sound recordings from a microphone to implement auscultatory blood pressure estimation. The microphone may be part of the other sensors 425, which may be arranged to record blood pulses occurring in the digital artery. The BP logic 419 may analyze the sound recordings in relation to pressure data received from the bladder 406 (due to a pressure sensor in the bladder 406) to determine a pressure when Korotkoff sounds begin and end. If the pressure in the bladder 406 is decreasing during this time, the pressure corresponding to the beginning of the Korotkoff sounds may be an estimate of the SBP, whereas the pressure corresponding to the ending of the Korotkoff sounds may be an estimate of the DBP.

In some embodiments, the BP logic 419 may determine the MAP, SBP and DBP using oscillometry. The determination of the MAP, SBP and DBP may be similar to the applanation tonometry techniques but the pressure sensor measurements may be used instead of the capacitive measurements of the TSA 410. For example, the pressure sensor included in the bladder 406 may measure pressure changes due to blood flow in the digital artery pressing the finger on the bladder 406. The pressure corresponding to when a maximum amplitude of a pressure pulse may be an estimate of the MAP. Subsequently, the BP logic 419 may determine the SBP and DBP through one or more regressions.

In some embodiments, the BP logic 419 may perform BP estimations using all three techniques. The BP estimations from the three different techniques may then be compared to determine a closest estimation of the user's BP at the digital artery.

The control logic 417 may receive diagnostic data from the other sensors 425, which may include a temperature sensor, accelerometer, PPG, and microphone. The data may be analyzed to determine if any of the measurements are outside of established thresholds and, if so, response accordingly. For example, if accelerometer data shows that the finger was moving more than desired during a blood pressure reading, the control logic 417 may reject that reading. Additionally, the control logic 417 may determine the user's HR, RR, and/or SpO2 based on PPG sensor data. Lastly, temperature data may be used to adjust any blood pressure estimations if the temperature is outside of an established range.

Communication logic 421 provides communication protocols for wireless communication with reader 435 via antenna 423. In one embodiment, communication logic 421 provides backscatter communication via antenna 423 when in the presence of an electromagnetic field 451 output from reader 435. In one embodiment, communication logic 421 operates as a smart wireless radio-frequency identification ("RFID") tag that modulates the impedance of antenna 423 for backscatter wireless communications. The various logic modules of controller 415 may be implemented in software/firmware executed on a general purpose microprocessor, in hardware (e.g., application specific integrated circuit), or a combination of both.

The illustrated embodiment also includes reader 435 with a processor 443, an antenna 445, and memory 437. Memory 437 includes data storage 439 and program instructions 441. As shown reader 435 may be disposed outside of device 400, but may be placed in its proximity to charge device 400, send instructions to device 400, and/or extract data from device 400. In one embodiment, reader 435 may resemble a hand held portable device that provides a holder or case for the device 400.

External reader 435 includes the antenna 445 (or group of more than one antennae) to send and receive wireless signals 451 to and from device 400. External reader 435 also includes a computing system with the processor 443 in communication with the memory 437. Memory 437 is a non-transitory computer-readable medium that can include, without limitation, magnetic disks, optical disks, organic memory, and/or any other volatile (e.g., RAM) or non-volatile (e.g., ROM) storage system readable by the processor 443. Memory 437 can include a data storage 439 to store indications of data, such as data logs (e.g., user logs), program settings (e.g., to adjust behavior of device 400 and/or external reader 435), etc. Memory 437 can also include program instructions 441 for execution by processor 443 to cause the external reader 435 to perform processes specified by the instructions 441. For example, program instructions 441 can cause external reader 435 to provide a user interface that allows for retrieving information communicated from device 400 or allows transmitting information to device 400 to program or otherwise select operational modes of device 400. External reader 435 can also include one or more hardware components for operating antenna 445 to send and receive wireless signals 451 to and from device 400.

External reader 435 can be a smart phone, digital assistant, or other portable computing device with wireless connectivity sufficient to provide the wireless communication link 451. External reader 435 can also be implemented as an antenna module that can be plugged into a portable computing device, such as in an embodiment where the communication link 451 operates at carrier frequencies not commonly employed in portable computing devices. In some embodiments, the external reader 435 may prompt a user of the device 400 to prepare for a BP reading, which may provide the user a moment to position the finger at an elevation equal with their heart. Additionally, while the BP reading is being performed, the external reader 435 may provide a distraction to the user. For example, the distraction could take the form of a news article, current weather conditions, a game, or display heart beat waveforms and BP measurements.

Figure 5:
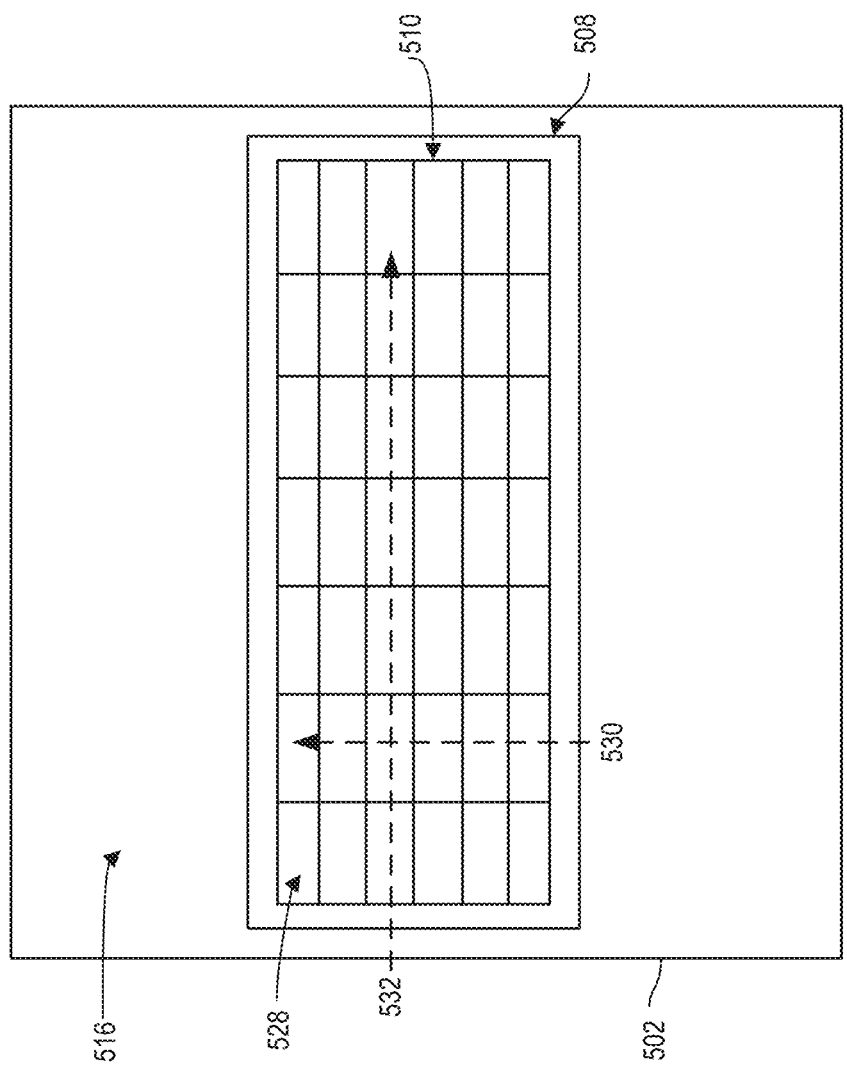
FIG. 5 is a plan view of a tactile sensor array 510 in accordance with an embodiment of the present disclosure.

FIG. 5 is a plan view of a tactile sensor array 510 in accordance with an embodiment of the present disclosure. The tactile sensor array (TSA) 510 may be an example of the TSAs 110, 210, 310, and/or 410. The illustrated embodiment of TSA 510 may include a plurality of capacitive sensors 528 arranged into an array having columns 530 and rows 532. In some embodiments, a substrate 508 may provide mechanical support for the TSA 510, and may be mounted or disposed on an inner surface 516 of a cuff 502. In some embodiments, the TSA 510 may have a semi-circumferential shape to for or fit around at least a portion of a finger, and or to an inner surface of a cuff, such as the cuff 102. In other embodiments, the TSA 510 may be flexible so that it can conform to the finger.

Each capacitive sensor 528 may be formed from a metal-insulator-metal capacitor, with the insulator capable of being deformed in the presence of pressure. Due to the deformation, e.g., flattening, of the insulator, the capacitance of the individual capacitive sensor 528 may change. For example, if a capacitive sensor 528 flattens, then the distance between the two conductors decreases, which increases the capacitance of the sensor 528. On the other hand, if the capacitive sensor 528 is stretched so that the distance between the two conductors increases, then the capacitance decreases. Additionally, if a capacitive sensor 528 is bent, the edges of conductors that form the two electrodes may move closer together, which may also affect the capacitance. By measuring the amount of change of the capacitance, increase in capacitance for example, an indicative amount of pressure being applied to the capacitive sensor 528 may be determined.

In some embodiments, the columns 530 may be arranged to be parallel with a digital artery. In such an embodiment, several instances of the capacitive sensors 528 in a same column may be aligned with the digital artery. In some embodiments, the number of columns may be greater than the number of rows to ensure that the TSA 510 overlays the desired digital artery when a finger-wearable device is worn by a user. While FIG. 5 shows 7 columns and 6 rows, other numbers of columns and rows may be implemented, such as 10 columns and three rows. Additionally, the pitch between adjacent columns 530 may be such that the distance between the columns may provide for a single column to overly the digital artery. For example, the pitch between columns 530 may be 0.75 mm in some embodiments. However, due to inexact alignment of the TSA 510 with a digital artery, instances of use may have multiple columns 530 at least partially overlapping the digital artery.

FIGS. 6A and 6B are a cross-sectional view and a plan view, respectively, of a TSA 610 in accordance with an embodiment of the present disclosure. TSA 610 may be an example of the TSA 110, 210, 310, 410 and/or 510. The TSA 610 includes a plurality of capacitive sensors 628 that form an array. The array of capacitive sensors 628 may be arranged into a grid having rows and columns. The illustrated embodiment of the TSA 610 includes a plurality of layers that combine to form each of the plurality of capacitive sensors 628, see FIG. 6A. The plurality of layers includes a support layer 646, a first electrode layer 644, an dielectric pillar layer 642, a second electrode layer 640, a protective layer 638, and a shield layer 636. The support layer 646 may provide mechanical support to the various other layers of the TSA 610. Additionally, the support layer 646 may be disposed on a substrate, such as the substrate 108, when the TSA 610 is mounted in a finger wearable cuff. On the other side of the TSA 610, the shield layer 636 may be finger facing, and may provide some protection of the internal layers of the TSA 610 from the finger. Additionally, the shield layer 636 may reduce parasitic capacitance formed between the finger and the first and second electrodes layers 644 and 640.

The first electrode layer 644 may form one side of a metal-insulator-metal (MIM) capacitor, which form each of the capacitive sensors 628. In some embodiments, the first electrode 644 may be pixelated for each of the plurality of capacitive sensors 628. The first electrode 644 may be formed from a conductive material, such as a metal or conductive polymer. Additionally, each electrode in the first electrode layer 644 may be individually coupled to traces that provide respective outputs for the capacitive sensors 628.

The second electrode layer 640 may be the second conductive layer in the MIM capacitor that forms the capacitive sensors 628. The second electrode layer 628 may be formed from the same or similar materials as the first electrode layer 644. While not shown, the second electrode layer 640 for each capacitive sensor 628 may be coupled to a conductive trace that provides an electric coupling to each capacitive sensor 628 so that the capacitance of each capacitive sensor 628 may be individually measured.

The dielectric pillar layer 642 may include a plurality of separate and individual pillars formed into an array, and which may form the insulator layer in the MIM capacitor. While the dielectric pillar layer 642 is shown to be formed from individual pillars, the layer 642 may also be formed from a continuous layer of soft material with the pixelated first and second electrode layers 640 and 644 formed on opposing sides. Each of the individual pillars may be disposed between the first and second electrode layers 644 and 640. Additionally, each of the individual pillars may be deformable so that they are able to decrease in height due to pressure, or even extend in height if pulled. The deformation of the individual pillars may change the capacitance of each of plurality of dielectric pillars. Additionally, the first and second electrode layers 640 and 644 may deform in gaps between adjacent capacitive sensors 628, where the deformation may also affect the capacitance of the sensor. The change in capacitance may be provided as a capacitance level signal in some embodiments, which may be indicative of the amount of pressure being applied. In some embodiments, each pillar of the dielectric pillar layer 642 may be formed from a soft, flexible dielectric material, such as silicone for example.

The protective layer 638 may be disposed over the second electrode layer 640, and may provide some mechanical support and protection to the TSA 610. In some embodiments, the protective layer 638 may provide support to the electrical traces coupled to the second conductive layer 640 of each capacitive sensor 628. In some embodiments, the protective layer 638 may be formed from Kapton.

In some embodiments, the protective layer 638 may have slits 648 formed therein between adjacent capacitive sensors 628. In some embodiments, the slits 648 may be formed only in the column direction, e.g., aligned with the finger, to mechanically decoupled adjacent columns. By mechanically decoupling adjacent columns, the capacitive sensors 628 in the adjacent columns may be more sensitive to pressure changes in the digital artery. In some embodiments, the slits 648 may be formed in both the column and row directions, thereby mechanically decoupling the capacitive sensors 628 in both directions. Forming the slits 648 in both directions may provide additional mechanically decoupling and increases sensitivity to the capacitive sensors 628.

The plan view of TSA 610 shown in FIG. 6B shows the support layer 646, individual areas of the first electrode layer 640/644, individual dielectric pillars of the dielectric pillar layer 642, and the protective layer 638. The protective layer 638 is depicted by the transparent cross-hatching that covers the entirety of FIG. 6B. Slits 648 are shown to be formed between individual ones of the capacitive sensors 628 in both column and row directions, but some embodiments may only include slits 648 in one of the directions.

FIGS. 7A and 7B are a cross-sectional view and a plan view, respectively, of a TSA 710 in accordance with an embodiment of the present disclosure. The TSA 710 may be an example of the TSA 110, 210, 310, 410 and/or 510. The TSA 710 includes a plurality of capacitive sensors 728 arranged in a two-dimensional array. The two-dimensional array may be arranged in columns and rows, similar to the TSA 510, with the number of columns outnumbering the number of rows. The columns may be aligned longitudinally with a finger whereas the rows may be aligned circumferentially with the finger.

The illustrated embodiment of the TSA 710 includes a support layer 746, a first electrode layer 744, a dielectric pillar layer 742, a second electrode layer 750, and a protective layer 752. The support layer 746, first electrode layer 744, and dielectric pillar layer 742 may be similar to like layers of the TSA 610, and, as such, will not be discussed in detail for sake of brevity. The combined layers of the TSA 710 may form the plurality of capacitive sensors 720, which may be MIM capacitors formed from the first and second electrode layers disposed on opposite sides of a dielectric pillar of the dielectric pillar layer 742. Due to the deformable nature of the dielectric pillars, the capacitance of each of capacitive sensor 728 may change when the pressure or tension is applied to the capacitive sensors 728 of the TSA 710.

The second electrode layer 750 may be formed form a conductive cloth that extends across the TSA 710. The conductive cloth may provide the conductor for one side of the capacitive sensors 728 along with electrical traces from each capacitive sensor to receive data signals. The use of the conductive cloth may allow each capacitive sensor 728 freedom to move without the movement being transferred to an adjacent capacitive sensor.

The protective layer 752 may be a continuous layer disposed on the second electrode layer 750. The protective layer 752, which may be finger facing, may provide physical protection from interaction with the surrounding environment. In some embodiments, the protective layer 752 may be soft and flexible so not to restrict movement, e.g., compression, of the underlying dielectric pillar layer 742. For example, the protective layer 752 may be formed from silicone, polyurethane film, or other soft, flexible plastic.

The plan view of TSA 710 shown in FIG. 7B shows the support layer 746, individual areas of the first electrode layer 744, individual dielectric pillars of the dielectric layer 742, and the second electrode 750. The second electrode 750 is depicted by the transparent cross-hatching that covers the entirety of FIG. 7B.

Figure 8:
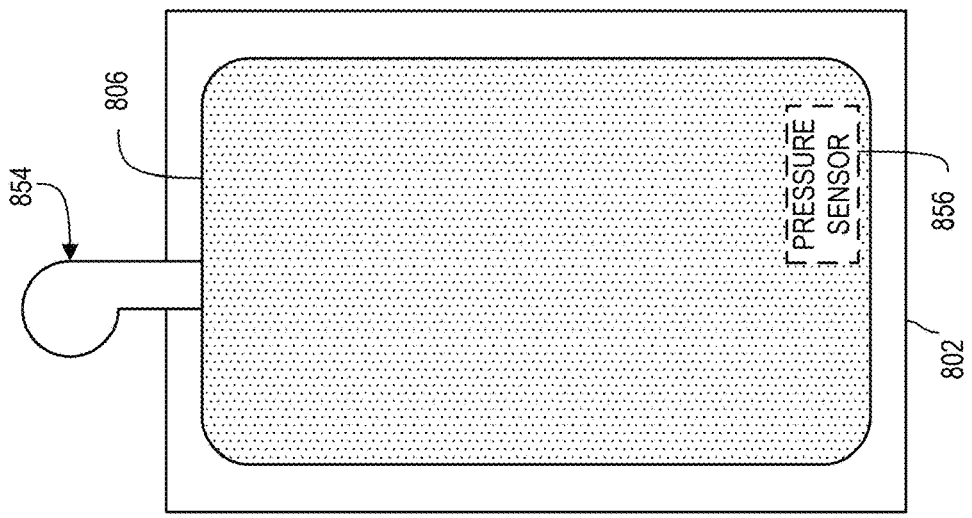
FIG. 8 is a bladder 806 in accordance with an embodiment of the present disclosure.

FIG. 8 is a bladder 806 in accordance with an embodiment of the present disclosure. The bladder 806 may be an example of the bladders 106, 206, and/or 406. The bladder 806 may be disposed on an inner surface 816 of a cuff 802. The illustrated embodiment of the bladder 806 may be coupled to an air pump 854 and a pressure sensor 856 may be disposed within the bladder 806. In some embodiments, the air pump 854 may pump air into the bladder 806 in response to a control signal from control circuitry 112, for example. The pressure sensor 856 may measure the pressure of the bladder 806, which may be provided to the control circuitry 112 in response. Additionally, the air pump 854 may deflate the bladder 806 at a desired controlled rate, also in response to a control signal from the control circuitry 112.

The bladder 806 may be formed from a flexible, stretchable material so that it inflates in response to introduction of air. For example, the bladder may be formed form a soft, stretchable plastic, polyurethane, or latex. In response to deflation, the bladder 806 may retake a taut form across the inner surface 816 so not to interfere with removal of the cuff 802 from a finger, or from inserting the finger into the cuff 802. In some embodiments, the bladder 806 may, in relation to the size of the finger, have a length that is 80% and a width that is 40% of a circumference of a finger. In other embodiments, the bladder 806 may be disposed on an inner surface of the cuff 802 on an opposite side from a TSA. The pressure sensor 856 may be disposed on the inner surface of the cuff 802 within the bladder 806. In some embodiments, the pressure sensor 856 may be a MEMS-type pressure sensor.

In operation, the air pump 854 may pump air into the bladder 806 in response to the control signal, and the pressure sensor 856 may monitor the internal pressure of the bladder 806. The internal pressure measurements may be provided to the control circuitry to determine when to cease inflation.

Figure 9:
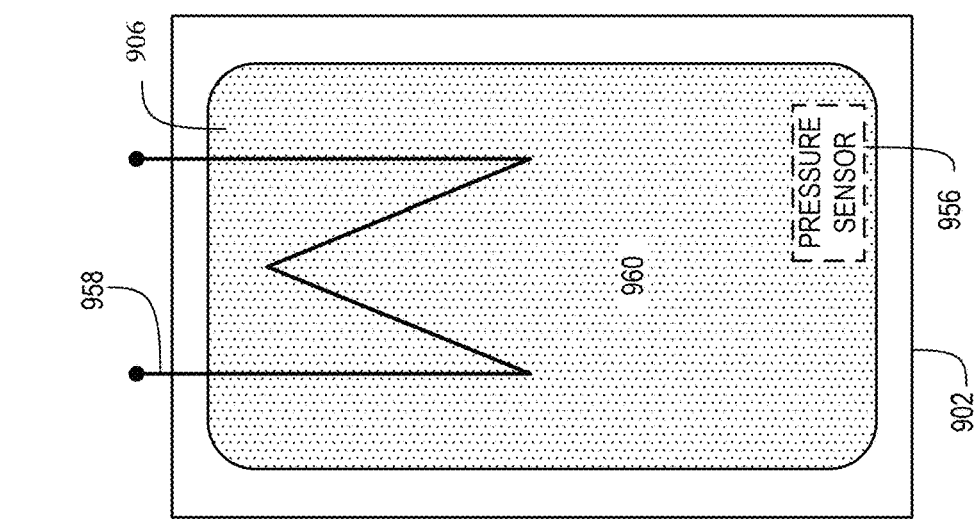
FIG. 9 is a bladder 906 in accordance with an embodiment of the present disclosure.

FIG. 9 is a bladder 906 in accordance with an embodiment of the present disclosure. The bladder 906 may be an example of the bladder 106, 206 and/or 406. The illustrated embodiment of the bladder 906 includes a heating coil 958, a refrigerant 960, and pressure sensor 956. The heating coil 958 may be disposed on an inner surface 916 of a cuff 902, and arranged within the bladder 906. The bladder 906 also being disposed on the inner surface of the cuff 902. To inflate the bladder 906, the refrigerant may undergo a phase transition from a liquid to a gaseous state.

The bladder 906 may be formed from similar materials as the bladder 806. However, the bladder 906 may be formed from materials that will not react with or be degraded by the refrigerant 960. In some embodiments, an inner surface of the bladder 906 may be coated with a non-reactive material to avoid degradation due to the refrigerant 960.

The refrigerant 960 may be in a liquid phase in a default state, but may undergo a phase transition to a gas phase when heated. The transition to the gas phase may inflate the bladder 906. The refrigerant may be a high boiling point refrigerant that may be converted to the gas phase at a temperature above body temperature, for example. For example, the refrigerant may be R-113 refrigerant, which is trichlorotrifluoroethane, that has a boiling point around 50° C.

In some embodiments, the heating coil 958 may be coupled to receive power from the control circuitry 112, for example. Providing power to the heating coil 958 may heat the refrigerant 960 to cause a phase change. The heating coil 958 may be formed from a metallic conductor that will not react with the refrigerant 960, or may be coated with a non-reactive material. Control circuitry 112 may provide the power to the heating coil 958 to heat the refrigerant 960 to at least its boiling point. Boiling the refrigerant will provide the needed gas to inflate the bladder 906.

The pressure sensor 956, which may be similar to the pressure sensor 856, may monitor the internal pressure of the bladder 906 and provide pressure data to control circuitry 112 in response. The control circuitry 112 may determine when to remove power from the heating coil 958 to deflate the bladder 906.

Figure 10:
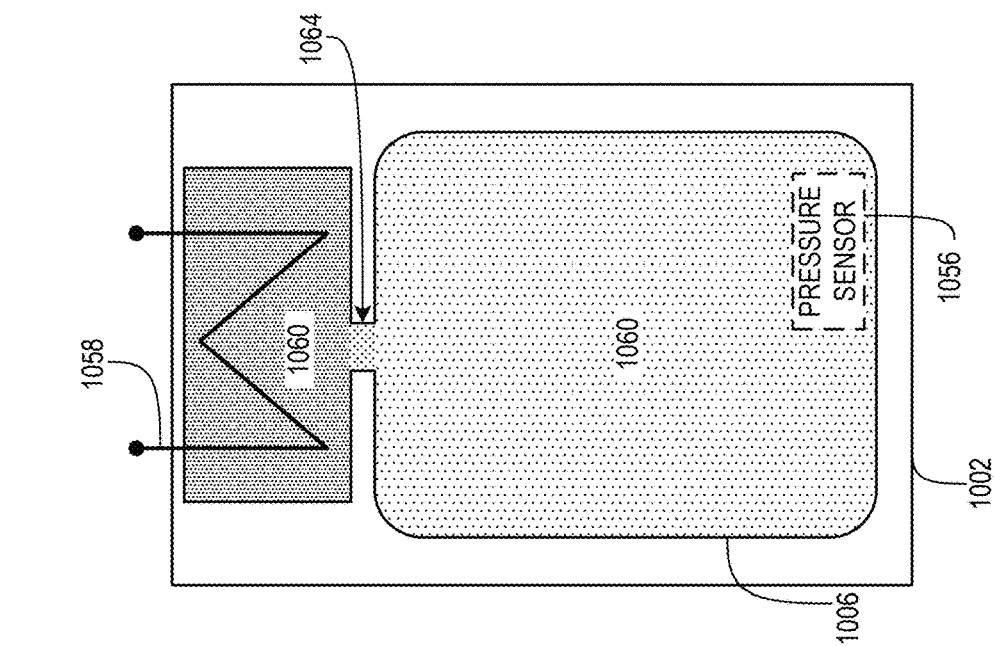
FIG. 10 is a bladder 1006 in accordance with an embodiment of the present disclosure.

FIG. 10 is a bladder 1006 in accordance with an embodiment of the present disclosure. Bladder 1006 may be an example of the bladder 106, 206, 406 and/or 906. The illustrated embodiment includes cuff 1002 and pressure sensor 1056. The bladder 1006 may be similar to the bladder 906 except that the refrigerant 1060 and heating coil 1058 may be disposed within a reservoir 1062 instead of within the bladder 1006. The reservoir 1062 may be fluidically coupled to the bladder 1006 via a conduit/channel 1064. Refrigerant 1060 may be in a liquid state in the reservoir 1062. When the heating coil 1058 receives power, the refrigerant 1060 within the reservoir 1062 may undergo the phase change to the gas phase, then move through the conduit 1064 into the bladder 1006 to inflate the bladder. While only one reservoir 1062 is shown, and is located at one end of the bladder 1006, in other embodiments, a second reservoir 1062 may be coupled to an opposite end of the bladder 1006. In such a configuration, the refrigerant 1060 may flow back into one of two reservoirs after returning to the liquid phase.

Figure 11:
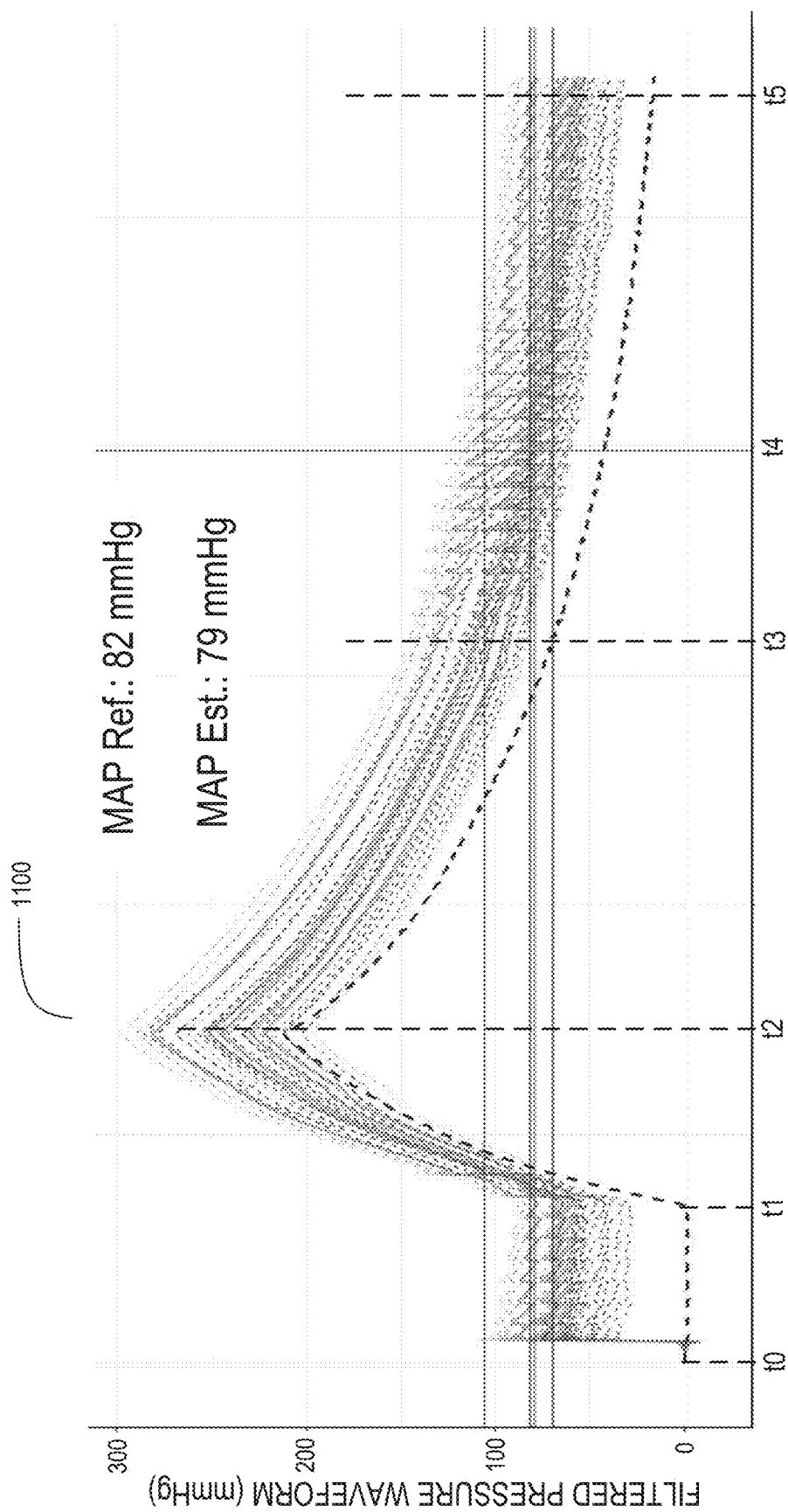
FIG. 11 is an example pressure plot 1100 in accordance with an embodiment of the present disclosure.

FIG. 11 is an example pressure plot 1100 in accordance with an embodiment of the present disclosure. The plot 1100 shows the relation of pressure and time when a finger-wearable blood pressure monitoring device, such as the device 100, performs a blood pressure reading operation. The plot 1100 will be used to further discuss the operation of the device 100, for example. While the plot 1100 may be described in relation to the device 100, the plot 1100 may also be used to illustrate the operation of the other embodiments discussed herein.

The plot 1100 shows the capacitance readings from all of the capacitive sensors from a TSA 110 in units of mmHg plotted against time. For example, the plot 1100 may show the capacitance readings of 30 individual capacitive sensors. Each pressure wave extracted from the capacitive measurements includes pulsatile components that occur when the pressure applied to the digital artery due to the TSA 110 being pressed against it is similar to the internal pressure in the digital artery, e.g., the blood pressure. The capacitance values from the TSA 110 may be converted to pressure due to the direct influence the pressure has on the capacitance sensors.

At time t0, the bladder 106 may be in a deflated state so that no or little pressure may be applied to the TSA 110 by a finger. At time t1, the bladder 106 may be inflated in response to one or more control signals from the control circuitry 112. The bladder 106 may be inflated to a pressure that is at least greater than a systolic BP of the user. The black dashed line shows the pressure in the bladder 106 as recorded by a pressure sensor, such as the pressure sensor 856. As the pressure reaches a desired maximum at t2, the control circuitry 112 may cause the pressure of the bladder 106 to decrease at a slow, controlled rate. For example, the bladder 106 may deflate at 2-3 mmHg/second. While the plot 1100 shows the pressure at time t2 to be around 200 mmHg and higher, which is above typical SBP readings, the maximum pressure may be less than 200 mmHg depending on the user's average SBP. However, in some embodiments, the bladder 106 may be inflated until occlusion of the digital artery is obtained.

Between times t1 and t2, the bladder 106 presses the finger onto the TSA 110 to cause the TSA 110 to deform a digital artery. For example, the TSA 110 may be pressed onto the skin and tissue that is directly over the digital artery. Pressing the TSA 110 firmly into the tissue over the digital artery may cause one or more columns of capacitive sensors to be pressed onto the tissue directly over the digital artery, for example. It may be desirable that the size of the capacitive sensors is such that a single capacitive sensor, or a column of sensors, is smaller than the diameter of the digital artery. A pitch between the columns may be less than the diameter of the digital artery as well. Sizing the capacitive sensors as such may assist with applanation tonometry. In general, it may be desirable to have at least one capacitive sensor centered on the digital artery.

As the pressure reaches a maximum at t2, the digital artery may be deformed to affect the blood flow within the digital artery. However, as the bladder 106 deflates, the pressure in the digital artery decreases accordingly. Additionally, the arterial wall being pressed on by the TSA 110 may begin to revert back to a normal condition, e.g., unobstructed. However, as the arterial wall gets close to its unobstructed condition, the arterial wall passes through a condition where it appears infinitely flat in regards to the size of the capacitive sensors pressing on it, e.g., the local radius of curvature approaches infinity. At this point, the transmural pressure may be zero. The transmural pressure being the difference between the internal pressure and the external pressure. The internal pressure would be the blood pressure, and as such the equal external pressure may provide a measurement of the blood pressure. When the local radius of curvature reaches this condition, the arterial wall may provide maximum pulsatile pressure due to blood flowing in response to heart beats. However, as the arterial wall moves through this state, the pulsatile pressure will begin to increase then decrease as shown by the increase in pulsatile pressures between t3 and t4, and the subsequent decrease in pulsatile pressures between t4 and t5.

At time t3, the arterial wall begins to near the local radius approaching infinity condition, at this time pulsatile pressure may begin to be measured by the TSA 110. The measured pulsatile pressures, which are due to the blood flow in response to heart beats, may begin to increase until time t4 due to the changing shape of the arterial wall. At time t4, the arterial wall may reach maximum flatness, e.g., the curvature with respect to a capacitive sensor approaches infinity, which provides the pulsatile pressure with the maximum amplitude. Further, between times t4 and t5 the pulsatile pressure will decrease until no pressure is applied by the bladder 106.

The applied pressure corresponding to the maximum pulsatile amplitude measured at time t4 may represent, or be an estimation of, the mean arterial pressure (MAP) at the digital artery. In some embodiments, the MAP estimation may be based on the capacitance changes of a single capacitive sensor, or a column of capacitive sensors. In other embodiments, the MAP estimation may be based on an average of all the capacitive sensors of the TSA 110. In yet another embodiment, the MAP estimation may be based on the capacitive sensor providing the lowest pressure reading. As noted in plot 1100, the MAP estimate is estimated to be 79 mmHg, whereas the reference MAP is 82 mmHg. The reference MAP may be a user's MAP based on a brachial BP measurement, for example, or based on standard BP guidelines.

Additionally or alternatively, auscultation may be used to estimate the blood pressure in the digital artery. To implement the auscultation, the microphone 226 may be used to record the sound of the blood pulses occurring in the digital artery. To perform blood pressure monitoring using the auscultation principles, the bladder 106 may be inflated to obtain occlusion of the digital artery. After the digital artery is occluded, the bladder 106 may be decreased in pressure at a slow and controlled rate. As the pressure decreases, the blood begins to flow in the digital artery causing audible pulses that may be recorded by the microphone 226. These pulses may be referred to as Korotkoff sounds. Pressures corresponding to the start and end of the Korotkoff sounds may estimate the SBP and DBP, respectively, of the user. The auscultatory technique may be implemented in addition to or as an alternative to the applanation tonometry technique.

Further, oscillometry may be implemented to estimate MAP, SBP and DBP at the digital artery based on the pulses in the blood flow that occur during the decrease in pressure by the TSA 110 in the digital artery. For example, pressure readings from a pressure of the bladder 106 may measure pressure pulses occurring due to the blood flow. The pressure pulses may show similar pressure measurements as shown in the plot 100. The pressure pulse with the maximum amplitude may be an estimate of the MAP, which may be used to estimate SBP and DBP.

Figure 12:
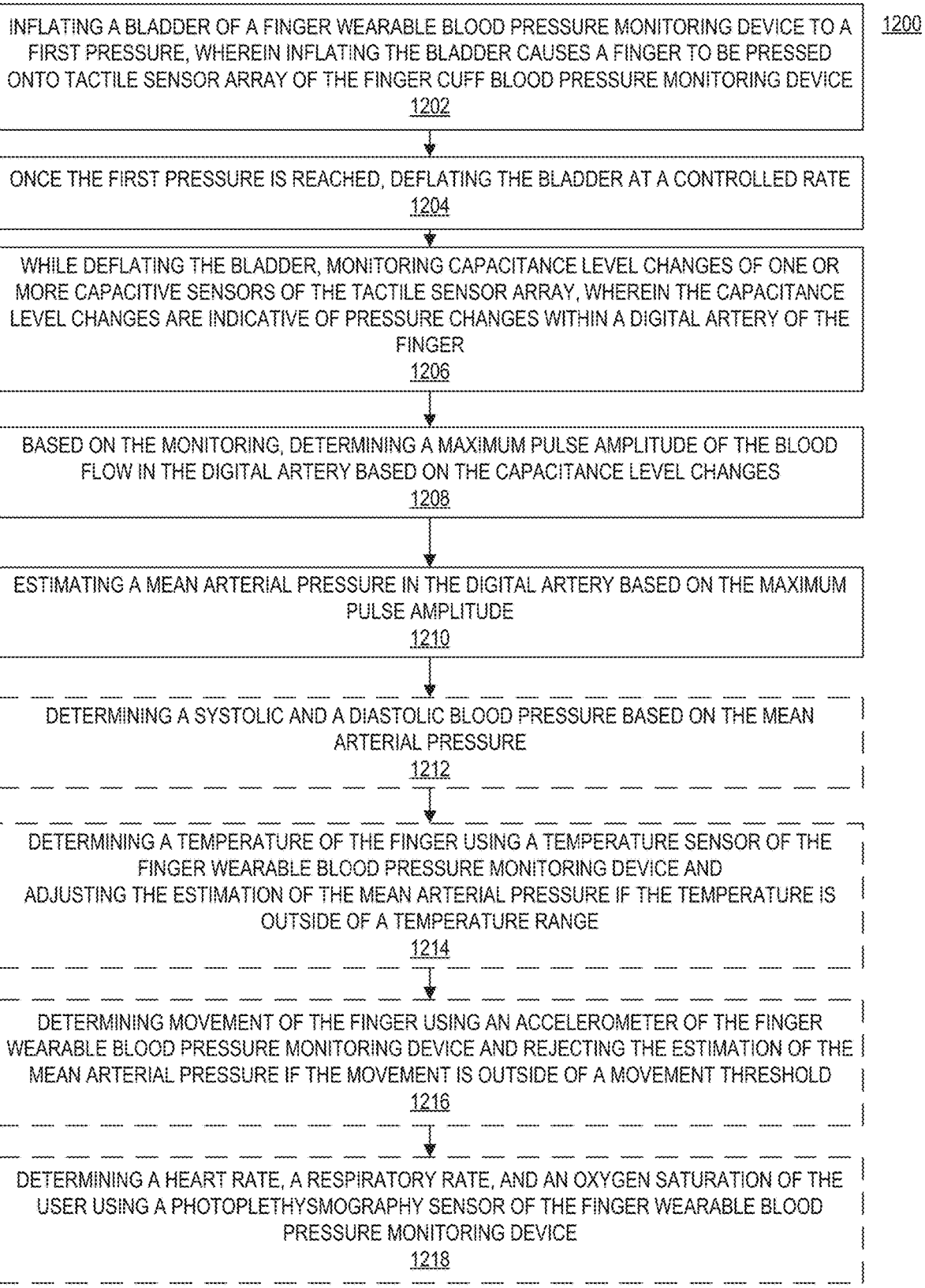
FIG. 12 is a method 1200 in accordance with an embodiment of the present disclosure.

FIG. 12 is a method 1200 in accordance with an embodiment of the present disclosure. The method 1200 may be an example operation of the device 100, 200, and/or 300. The method 1200 outlines some of the steps in determining at least the digital blood pressure of a user using a finger-wearable blood pressure monitoring device. In some embodiments, the device may implement applanation tonometry to determine the blood pressure. In other embodiments, oscillometry or auscultation may be implemented in addition to or instead of the applanation tonometry. While the method 1200 is discussed in terms of slowly deflating the bladder to determine the BP at the digital artery, the method 1200 may also be used during a slow, controlled inflation of the bladder.

The method may begin at step 1202 with inflating a bladder of a finger wearable blood pressure monitoring device to a first pressure. Inflating the bladder may cause a finger of a user to be pressed into a TSA of the device. In some embodiments, the first pressure may be a pressure at least greater than a SBP of the user. In other embodiments, the first pressure may be high enough to occlude blood flow in a digital artery of the finger.

The step 1202 may be followed by step 1204, which includes deflating the bladder at a controlled rate once reaching the first pressure. In some embodiments, the bladder may be deflated at a rate of 2 to 3 mmHg/s. The step 1204 may be followed by step 1206, which includes while deflating the bladder, monitoring capacitance level changes of one or more capacitive sensors of the tactile sensor array, wherein the capacitance level changes are indicative of pressure changes within a digital artery of the finger. While inflating the bladder may press the TSA into the finger so that the underlying digital artery is deformed or occluded, deflating the bladder in a controlled manner may allow for the changes in pressure internal to the digital artery due to the physical deformation of the artery in addition to the blood pressure to be measured.

The step 1206 may be followed by the step 1208, which includes based on the monitoring, determining a maximum pulse amplitude of the blood flow in the digital artery based on the capacitance level changes. The maximum pulse amplitude may be determined from the maximum capacitance changes measured by the TSA in response to the blood flow in the digital artery. The maximum capacitance changes may be measured when the local radius of curvature of the digital artery approaches infinity, which allows the arterial wall to move a maximum distance in response to the blood pressure.

The step 1208 may be followed by the step 1210, which includes estimating a mean arterial pressure in the digital artery based on the maximum pulse amplitude. The mean arterial pressure may be estimated from the applied pressure where the maximum pulse amplitude occurs. In some embodiments, the applied pressure where the maximum pulse amplitude occurs may be an average of all capacitive sensors of the TSA, or may be based on a lowest pressure recorded by the TSA. In some embodiments, the pulsatile waves measured by the TSA may be analyzed in the frequency domain to determine the mean arterial pressure.

Any of the steps 1202-1210 may be followed by optional steps 1212 through 1218, which include the measurement of other diagnostic variables. Additionally, the steps 1212-1218 may be performed in any order and/or in isolation of any of the other steps. For example, step 1212 may include determining a systolic and diastolic blood pressure based on the mean arterial pressure. Optional step 1214 may be performed as well, and includes determining a temperature of the finger using a temperature sensor and adjusting the estimate of the mean arterial pressure if the temperature is outside of a temperature range. Additionally, optional step 1216 may be performed, which includes determining movement of the finger using an accelerometer and rejecting the estimation of the mean arterial pressure if the movement is outside of a movement threshold. Further, step 1218 may be performed, which includes determining a heart rate, a respiratory rate, and an oxygen saturation of the user using a PPG sensor of the finger wearable blood pressure monitoring device.

In addition to the process steps listed above, various other steps may be performed, such as transmitting the blood pressure data and other data to an external reader for displaying to the user and/or providing to a physician. In some embodiments, the data may be provided to the physician through an associated application or via the user's electronic medical records.

The order in which some or all of the process blocks appear in process 1200 should not be deemed limiting. Rather, one of ordinary skill in the art having the benefit of the present disclosure will understand that some of the process blocks may be executed in a variety of orders not illustrated, or even in parallel.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A finger-wearable blood pressure monitoring device, comprising:
    a cuff;
    a bladder disposed proximate to the cuff;
    a pressure sensor coupled to the bladder to detect pressure changes within a digital artery of a finger due to blood flow when the finger wears the finger-wearable blood pressure monitoring device, wherein the bladder extends partially along a circumference of an inner surface of the cuff and is disposed between the pressure sensor and the finger when the finger wears the finger-wearable blood pressure monitoring device, and wherein the pressure sensor is disposed on the inner surface of the cuff; and
    control circuitry coupled to the pressure sensor to receive pressure data representative of the pressure changes and determine a blood pressure based on the pressure data.

2. The finger-wearable blood pressure monitoring device of claim 1, wherein the bladder is inflatable to cause the finger to be pressed onto the cuff when the bladder is inflated.

3. The finger-wearable blood pressure monitoring device of claim 2, wherein the bladder is coupled to a pump configured to pump air into the bladder to inflate the bladder.

4. The finger-wearable blood pressure monitoring device of claim 2, further including a heating element and a refrigerant disposed inside the bladder, wherein the heating element is activated to cause the refrigerant to change from a liquid state to a gas state to inflate the bladder.

5. The finger-wearable blood pressure monitoring device of claim 2, further including a heating element included in a reservoir coupled to the bladder.

6. The finger-wearable blood pressure monitoring device of claim 1, wherein a mean arterial pressure is determined based on the pressure data.

7. The finger-wearable blood pressure monitoring device of claim 1, further comprising a tactile sensor array positioned to additionally detect the pressure changes based on changes to capacitance values, the tactile sensor array including a plurality of capacitive sensors formed from a plurality of layers, the plurality of layers including:
    a first conductive layer disposed on a substrate;
    a second conductive layer; and
    deformable dielectric pillars disposed between the first and second conductive layers, wherein each deformable dielectric pillar in combination with the first and second conductive layers form an instance of a capacitive sensor of the tactile sensor array, and wherein a deformation of the deformable dielectric pillars causes the capacitance values of the capacitive sensor to change.

8. The finger-wearable blood pressure monitoring device of claim 7, wherein the plurality of layers further include:
    a protective layer disposed on the second conductive layer, and wherein slits are formed in at least the protective layer to reduce mechanical coupling between instances of the plurality of capacitive sensors.

9. The finger-wearable blood pressure monitoring device of claim 7, wherein the plurality of layers further include a dielectric layer disposed on the second conductive layer.

10. The finger-wearable blood pressure monitoring device of claim 7, wherein the second conductive layer is a continuous layer of conductive cloth.

11. The finger-wearable blood pressure monitoring device of claim 1, wherein the cuff has a shape to fit at least partially around the finger, and wherein the cuff is adjustable to fit around fingers of different sizes.

12. The finger-wearable blood pressure monitoring device of claim 1, further comprising a temperature sensor disposed proximate to the cuff to determine a temperature of the finger when the cuff is worn by a user, and wherein the temperature sensor is further coupled to the control circuitry to provide the temperature to the control circuitry.

13. The finger-wearable blood pressure monitoring device of claim 1, further comprising a microphone disposed proximate to the cuff to record blood pulses in the digital artery, and wherein the microphone is further coupled to the control circuitry to provide the recorded blood pulses to the control circuitry.

14. The finger-wearable blood pressure monitoring device of claim 1, further comprising a photoplethysmography sensor disposed proximate to the cuff to emit light into the finger and measure an amount of light exiting the finger when the finger wears the finger-wearable blood pressure monitoring device, and wherein the photoplethysmography sensor is further coupled to the control circuitry to provide the measurement of the amount of light exiting the finger to the control circuitry.

15. The finger-wearable blood pressure monitoring device of claim 1, wherein the cuff and the control circuitry are disposed inside a glove finger or mounted to a stationary surface or a handheld device.

16. A finger cuff blood pressure measuring apparatus, comprising:
    a cuff;
    a bladder disposed proximate to the cuff;
    a pressure sensor coupled to the bladder to detect pressure changes within a digital artery of the finger due to blood flow when the finger is inserted in the cuff, wherein the bladder extends partially along a circumference of an inner surface of the cuff and is disposed between the pressure sensor and the finger when the finger is inserted in the cuff, and wherein the pressure sensor is disposed on the inner surface of the cuff; and
    control logic coupled to the pressure sensor, the control logic including at least one non-transitory machine-accessible storage medium that provides instructions for obtaining a blood pressure estimation that, when executed by the control logic, cause the apparatus to:

determine, based on pressure data received from the pressure sensor, pressure changes due to blood flow in the digital artery; and based on the pressure changes, determine a blood pressure.

17. The finger cuff blood pressure measuring apparatus of claim 16, wherein the at least one non-transitory machine-accessible storage medium further provides instructions that, when executed by the control logic, cause the apparatus to;

perform frequency domain analysis on the pressure data to determine a mean arterial pressure, a systolic blood pressure, and a diastolic blood pressure at the digital artery.

18. The finger cuff blood pressure measuring apparatus of claim 16, wherein, the bladder is inflatable and positioned on the cuff to be pressed against the finger when the bladder is inflated, and wherein the at least one non-transitory machine-accessible storage medium further provides instructions that, when executed by the control logic, further cause the apparatus to:

inflate the bladder to a first pressure, the first pressure at least greater than a systolic blood pressure of the user;

upon reaching the first pressure, deflate the bladder at a controlled rate; and while the bladder is deflating, record pressure data from the pressure sensor to determine a maximum pulsatile due to blood flow in the digital artery.

19. The finger cuff blood pressure measuring apparatus of claim 16, wherein the at least one non-transitory machine-accessible storage medium further provides instructions that, when executed by the control logic, further cause the apparatus to:

determine a mean arterial pressure at the digital artery based on the pressure data;

compare the mean arterial pressure to a threshold mean arterial pressure value; and provide an alert if the mean arterial pressure is above the threshold mean arterial pressure value, wherein the alert is provided via an external reader.

20. The finger cuff blood pressure measuring apparatus of claim 16, further comprising a temperature sensor disposed proximate to the cuff to determine a temperature of the finger, and wherein the at least one non-transitory machine-accessible storage medium further provides instructions that, when executed by the control logic, further cause the apparatus to:

determine whether the temperature of the finger is below a temperature threshold; and instruct the user to warm up their finger if the temperature is determined to be below the temperature threshold.

* * * * *